(12) United States Patent
Middeldorp

(10) Patent No.: US 8,241,639 B2
(45) Date of Patent: Aug. 14, 2012

(54) EXTRACELLULAR DOMAINS OF EPSTEIN BARR VIRUS (EBV) TUMOR-ASSOCIATED LATENT MEMBRANE PROTEINS

(75) Inventor: Jaap Michiel Middeldorp, Oss (NL)

(73) Assignee: Cyto-Barr B.V., Bergen (NL)

( * ) Notice: Subject to any disclaimer, the term of this patent is extended or adjusted under 35 U.S.C. 154(b) by 50 days.

(21) Appl. No.: 12/857,930

(22) Filed: Aug. 17, 2010

(65) Prior Publication Data

US 2011/0064759 A1    Mar. 17, 2011

Related U.S. Application Data

(63) Continuation of application No. 11/284,879, filed on Nov. 22, 2005, now Pat. No. 7,811,581.

(51) Int. Cl.
*A61K 39/25* (2006.01)
*A61K 39/00* (2006.01)

(52) U.S. Cl. .................... 424/230.1; 424/185.1

(58) Field of Classification Search ............. None
See application file for complete search history.

(56) References Cited

FOREIGN PATENT DOCUMENTS

| WO | WO 90/04176 | 4/1990 |
| WO | WO 92/00525 | 1/1992 |
| WO | WO 96/20723 | 7/1996 |
| WO | WO 01/37868 | 5/2001 |

OTHER PUBLICATIONS

Bharadwaj et al., Expert Rev. Vaccines, 2002, 1(4):467-476.*
Duraiswamy et al., Blood, Apr. 15, 2003, 101(8):3150-3156.*
Paramita et al., Journal of Medical Virology, 2011, 83:665-678.*
Khanna R. et al., IdentificatiOn of Cytotoxic T Cell Epitopes within Epstein-Barr Virus (EBV) Oncogene Latent Membrane Protein 1 (LMP1): Evidence Forhla A1 Supertype-Restricted Immune Recognition of EBV-Infected Cells by LMP1-Specific Cytotoxic T. Lymphocytes; European Journal of Immunology, Weinheim, DE, vol. 28, No. 2 Feb. 1998; pp. 451-458.
Strockbine L. et al., The Epstein-Barr virus BARF1 Gene Encodes a Novel, Soluble Colony-stimulating factor-1 Receptor; Journal of Virology; Mar. 1998, vol. 72, No. 5; pp. 4015-4021; Seattle WA 98105.
Meij P. et al., Restricted Low-Level Human Antibody Responses Against Epstein-Barr Virus (EBV)-Encoded Latent Membrane Protein 1 in a Subgroup of Patients with EBV-Associated Diseases; The Journal of Infectious Diseases; US, May 1999, vol. 179, No. 5, pp. 1108-1115.
Leen A. et al., Differential Immunogenicity of Epstein-Barr Virus Latent-Cycle Proteins for Human CD4 (+) T-Helper 1 Responses; Journal of Virology, US, Sep. 2001, vol. 75, No. 18, pp. 8649-8659.
Rowe, David T., Epstein-Barr Virus Immortalization and Latency; Frontiers in Bioscience, Mar. 15, 1999; vol. 4, No. Cited Mar. 16, 1999; pp. D346-D371; HTTP://www.bioscience.org/1999/V4/D/Rowe/FULLTEXT.HTM.
Khanna, R. et al. Identification of Cytotoxic T Cell Epitopes Within Epstein-Barr Virus (EBV) Oncogene Latent membrane Protein 1(LMP1): Evidence for HLA A1 Supertype-Restricted Immune Recognition of EBV-Infected Cells by LMP1-Specific Cytotoxic T Lymphocytes, Eur J Immunology, Weinham, DE, vol. 28, No. 2 Feb 1998; pp. 451-458.
Stockbrine, L. et al., The Epstein-Barr Virus BARF1 Gene Encodes a Novel, Soluble Colony-Stimulating Factor-1 Receptor, J. Virology, Mar. 1998, vol. 72, No. 5; pp. 4015-4021.
Meji, P. et al., Restricted Low Level Human Antibody Responses Against Epstein Barr Virus (EBV) Encoded Latent Membrane Protein 1 in a Subgroup of Patients With EBV-Associated Diseases, J. of Infectious Disease, US, May 1999, vol. 179, No. 5, pp. 1108-1115.
Leen, A., et al., Differential Immunogenicity of Epstein Barr Virus Latent Cycle Proteins for Human CD4 (+) T-Helper 1 Responses, J. of Virology, US, Sep. 2001, vol. 75, No. 18, pp. 8649-8659.
Rowe, David T., Epstein Barr Virus Immortalization and Latency: Frontiers in Bioscience, Mar. 15, 1999, vol. 4, No. Cited Mar. 16, 1999; pp. D346-D371; http://www.bioscience.org/1999/V4/D/Rowe/FULLTEXT.htm.

* cited by examiner

*Primary Examiner* — Stacy B. Chen
(74) *Attorney, Agent, or Firm* — Hoffmann & Baron, LLP

(57) ABSTRACT

Described are a method for the identification of extracellular epitopes of Epstein Barr virus (EBV) encoded membrane proteins, expressed on the cuter cell surface of EBV-transformed mammalian cells, methods for the selection and preparation of antibody reagents specific for the said epitopes, as well as peptides, including extracellular domains of Epstein Barr Virus encoded tumour cell associated membrane proteins, the use of said peptide for immunization and therapeutic vaccination to induce antibodies and T-cells reactive with said domains, the use of said antibody reagents for the production of targeting cells, tumour cell purging and as diagnostic for and medicament against EBV-mediated malignant cell growth.

9 Claims, 11 Drawing Sheets

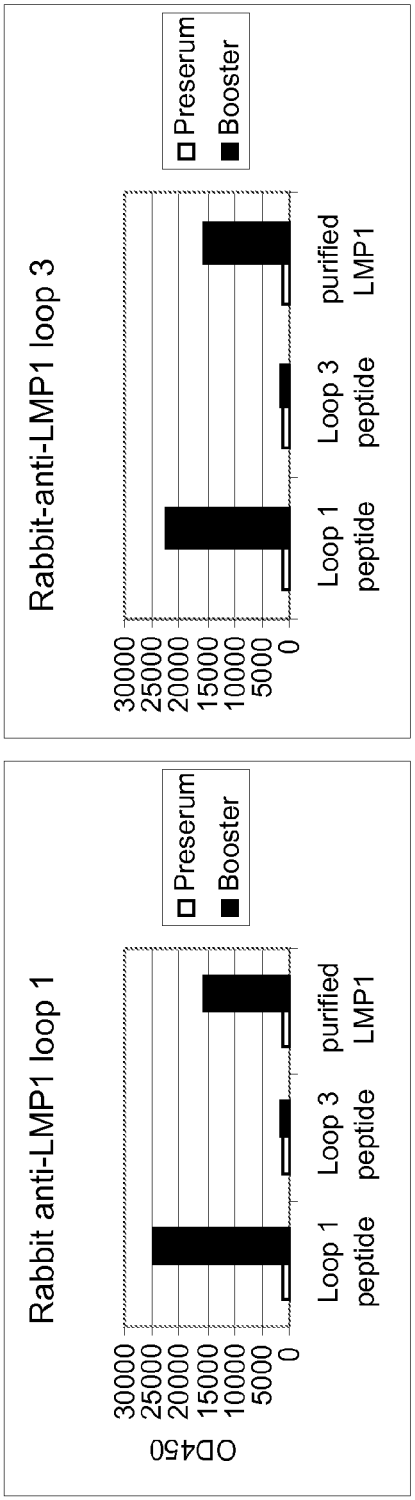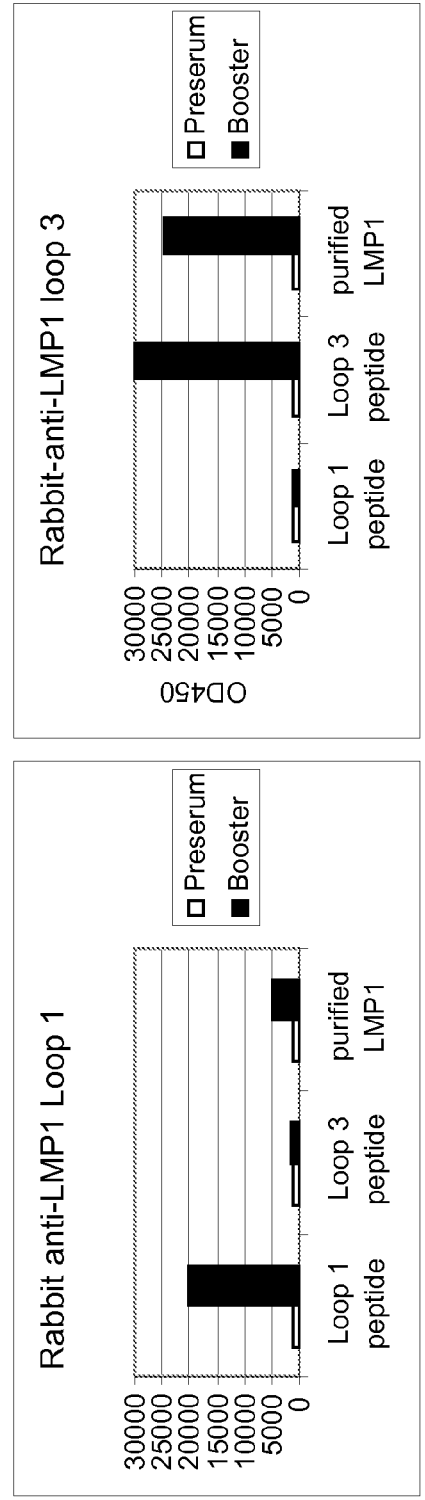
Fig. 3A  Fig. 3B  Fig. 3C  Fig. 3D

EXTRACELLULAR DOMAINS OF EPSTEIN BARR VIRUS (EBV) TUMOR-ASSOCIATED LATENT MEMBRANE PROTEINS

CROSS-REFERENCE TO RELATED APPLICATIONS

The present application is a continuation of U.S. application Ser. No. 11/284,879 filed Nov. 22, 2005 which has issued as U.S. Pat. No. 7,811,581, which claims priority to U.S. application Ser. No. 10/470,753 entitled, "METHOD FOR THE IDENTIFICATION OF EXTRACELLULAR DOMAINS OF EPSTEIN BARR VIRUS (EBV) TUMOR-ASSOCIATED LATENT MEMBRANE PROTEINS AND FOR THE SELECTION OF ANTIBODY REAGENTS REACTIVE THEREWITH," filed on Dec. 12, 2003, now abandoned, which itself claims priority from PCT/E202/00997 having an international filing date of Jan. 30, 2002.

TECHNICAL FIELD OF THE INVENTION

The present invention relates to a method for identification of extracellular epitopes of Epstein Barr Virus (EBV) encoded membrane proteins, to a method for the selection of antibody reagents reactive with the said epitopes, to novel peptides, comprising extracellular domains of Epstein Barr Virus (EBV) encoded latency- and tumour-associated membrane proteins, to nucleotide sequences encoding said peptides, vectors comprising said nucleotide sequences, to antibody reagents reactive with said extracellular domains and to the use of the peptides, nucleotide sequences encoding said peptides and said antibody reagents for the preparation of a medicament, in particular against EBV driven malignant growth, for vaccination and immunotherapy against Epstein Barr Virus infection, and to the use of the antibody reagents as diagnostic for the detection of EBV transformed (tumour) cells in vitro and in vivo. Furthermore, modifications of these peptides and antibody reagents to increase their diagnostic and therapeutic efficacy are included.

DESCRIPTION OF RELATED ART

Epstein-Barr Virus (EBV) is a ubiquitous human herpes virus that was first discovered in association with the African (endemic or e) form of Burkitt's lymphoma (BL). Subsequently the virus was also found associated with nasopharyngeal carcinoma (NPC) and was shown to be the causative agent of infectious mononucleosis (IM). Infection usually occurs during early childhood, generally resulting in a subclinical manifestation, occasionally with mild symptoms. Infection during adolescence or adulthood, however, can give rise to IM characterised by the presence of atypical lymphocytes in the periphery. The bulk of these lymphocytes are T lymphocytes; however, included in their number are a small population of B lymphocytes infected by EBV. The infection of B-lymphocytes may also be accomplished in vitro. Such cells become transformed and proliferate indefinitely in culture and have been referred to as "immortalised", "latently infected" or "growth transformed". As far as is known, all individuals who become infected with EBV remain latently infected for life. This is reflected by the lifelong continuous presence of small numbers of EBV-genome positive transformed B-cells among the circulating peripheral blood lymphocytes and the continuous but periodic shedding of virus in the oropharynx.

In the vast majority of cases EBV infection results in a lymphoproliferative disease that may be temporarily debilitating, but is always benign and self-limiting. In certain immunosuppressed individuals, however, the result can be uncontrolled lymphoproliferation leading to full-blown malignancy. This occurs in individuals who are immunosuppressed intentionally, particularly individuals receiving organ or bone marrow transplants who are treated with cyclosporine A, or opportunistically, as in the case with individuals infected with HIV, or genetically, as in the case of affected males carrying the XLP α-linked lymphoproliferative syndrome) gene. In these cases the resulting malignancies derive from the polyclonal proliferation of EBV-infected B cells. In addition, in such patients uncontrolled epithelial replication of the virus is detectable in lesions of oral hairy leukoplakia. Thus, the immune response plays a central role in the control of EBV infection.

Furthermore, EBV is associated with a still growing number of malignancies in otherwise immunocompetent individuals, which can be either of lymphoid or epithelial origin. Examples are Burkitt's Lymphoma (BL), B-cell non-Hodgkin Lymphoma, (B-NHL), extranodal T-/NK-cell Lymphoma (T/NK-NHL), Hodgkin's Disease (HD), Nasopharyngeal Carcinoma (NPC)) and Gastric Adenocarcinoma (GC) (Baumforth et al, J. Clin. Pathol.: Mol. Pathol. (1999) 52; 307-322).

For many years, Burkitt's lymphoma (BL) derived cell lines and EBV-transformed peripheral blood B-cells, also named lymphoblastoid cell lines (LCL) were considered to be the prototype model system for studying EBV-mediated transformation and oncogenesis. During recent years the entire DNA sequence of prototype virus strain, B95-8, has been determined. Analysis of this sequence has resulted in the identification of more than 80 open reading frames (Baer et al., Nature 310; 207-211 (1984)), the expression of which has been studied extensively in vitro and in vivo.

Interestingly, in human malignancies only a limited set of these genes is actively expressed, which are called latent gene transcripts. Basically three different latent gene transcription patterns have been observed in the various EBV-associated malignancies. These patterns are called latency type I, type II and type III. Recent data show the presence of additional transcripts complicating this typing system (zur Hausen et al, Cancer Research, 60 (2000); 2745-2748 and European Patent Application No. 98200655.3).

Latency type I is characterised by the expression of Epstein Barr Nuclear Antigen 1 (EBNA-1; BKRF1) and the small non-coding RNA's Epstein Barr Early RNA 1 and 2 (EBER-1 and EBER-2). More recently a novel set of transcripts (BARTs), with potential protein coding capacity (BARF0, RPMS1 and A73) in a number of small open reading frames included within these transcripts, has been found in all cells expressing the latency type I pattern. Latency type II is characterised by the additional expression of Latent Membrane Protein 1 (LMP-1; BNLF1) and LMP-2A/-2B (BNRF1), in addition to the type I transcripts mentioned above. LMP2 transcripts can only be expressed when the viral genome is in the covalently closed circular form as these transcripts cross the terminal repeats on the viral genome and cannot be formed when the viral genome is in its linear "lytic" state. A membrane-spanning protein encoded within the BARF1 open reading frame was recently shown to be expressed preferentially in EBV+ epithelial tumours displaying either a latency type-I or a latency type-II phenotype (zur Hausen et al, Cancer Research, 60 (2000); 2745-2748 and European Patent Application No. 98200655.3). Latency type III is characterised by the expression of the nuclear antigens EBNA-2, EBNA-3A, EBNA-3B, EBNA-3C and EBNA-4 (also referred to as EBNA-2, -3, -4, -6 and -5 respectively), in addition to the type II program transcripts (Baumforth et al, J. Clin. Pathol.: Mol. Pathol. (1999) 52; 307-322, Cohen J I. New Engl. J. Mea. (2000) 343; 481-492). The expression of the different latency-associated transcription programs is influenced by host cell parameters, such as the level of methylation and cellular differentiation (Robertson E D, Curr. Top. Microbiol. Immunol. (2000) 249; 21-34). The association of different latency type profiles with the various EBV-associated malignancies has been determined in detail in recent years using either RNA (reverse) transcription-based or in situ hybridisation and immunchistochemical staining techniques. Using these types of analysis, type I latency is found in BL tumour cells in vivo and sporadic BL-derived cell lines in vitro (Baumforth et al, J. Clin. Pathol.: Mol. Pathol. (1999) 52; 307-322). Type II latency is found in NPC, EBV-positive cases of Hodgkin's Lymphoma, T-/NK-cell and B-cell non-Hodgkin lymphoma (T-/NK-/B-NHL) and rare thymic and parotid carcinomas in the immunocompetent host, whereas type III latency patterns are found in pre-malignant lymphoproliferations and immunoblastic lymphoma which mainly occur in immunocompromised individuals and in most BL and LCL lines cultured in vitro (Baumforth et al, J. Clin. Pathol.: Mol. Pathol. (1999) 52; 307-322). In immunocompromised patients sporadic leiomyosarcoma is also found which may express the type I or II pattern. EBV+ epithelial cancers like gastric adenocarcinomas, nasopharyngeal carcinoma and rare hepatocellular carcinomas in non-compromised patients were found to express a type I or II latency pattern, with the additional expression of BARF1 (zur Hausen et al, Cancer Research, 60 (2000) pp. 2745-2748, Brink et al, J. Clin. Microbiol. 36 (1998) pp. 3461-3469 and European Patent Application No. 98200655.3).

Thus, EBV-positive tumours are characterised by active expression of viral gene products, some of which comprise of membrane spanning proteins localised to the plasma membrane of the tumour cells. These latency-associated membrane antigens are potential targets for specific recognition of EBV+ tumour cells.

Following primary infection the host develops an effective and lifelong immune response to EBV. This response is dominated by effector B-cells producing antibodies to virus structural components (VCA and MA) and intracellular nuclear antigens (esp. EBNA) and by effector T-cells reactive with latency III associated nuclear antigens (esp. EBNA3 family) and several antigens associated with the lytic phase of viral gene expression. T-cell targets are derived from proteins expressed inside EBV+ cells following digestion by the proteasome complex and subsequent transport of small peptide fragments to the cell surface in the context of MHC-I and MHC-II molecules. Antibodies are directed to both conformational and/or linear epitope domains on intact or fragmented proteins released from EBV-infected cells.

T-cells recognising latency-III specific gene products are considered of major importance for life-long control over the potential outgrowth of EBV+ B-cells in vivo. Antibodies to the MA complex are considered to be important for virus neutralisation by preventing the binding of infectious virions to the EBV-receptor, i.e. CD21. Although in most EBV-infected individuals antibodies to the MA complex are detectable, which are capable of mediating the elimination of MA-expressing virus-producing cells in vitro, their contribution to eradication of EBV+ tumour cells in vivo is null because the EBV+ tumours do not express MA. Similarly, antibodies to other virus structural proteins are considered to be irrelevant for anti-tumour immune control.

In order to induce and maintain antibody and T-cell responses viral antigens are digested by phagocytic cells, so called antigen-presenting cells (APC's), which can display these antigens on their cell surface in either MHC-I/-II or I the form of intact protein (fragments) captured in immune complexes or by additional surface receptors. Upon encounter with EBV antigen-specific T- and or B-cells these APC provide stimulatory signals resulting in the generation of effector B- and T-cells.

Interestingly and surprisingly, there is hardly any antibody or T-cell reactivity detectable against the "non-self" latency-associated membrane proteins LMP1 and LMP2 in EBV-infected individuals. These proteins are therefore classified as sub-dominant. Until now, responses to the BARF1 protein have not been described in great detail. It is important to state that no (natural or in vitro generated) antibodies have been described till now that react with putative extracellular domains of the EBV-encoded latency-associated membrane antigens expressed on EBV-transformed tumour cells.

In immunodeficient patients with defective cellular immunity directed against the dominant antigens as described above (esp. in XLP-patients, transplant recipients and HIV-infected individuals), the immune system fails to eradicate EBV+ B-cells expressing the latency-III phenotype, thus allowing their uncontrolled outgrowth frequently resulting in malignant oligoclonal and monoclonal B-cell tumours.

In non-immunocompromised (immunocompetent) patients the process of tumour formation (pathogenesis) is much more complex and still largely unresolved, but is considered to involve the direct growth stimulation, immunomodulation and apoptosis resistance induced by EBV gene products expressed in these cells, in concerted action with or paralleled by deregulated host cell functions.

Interestingly, the tumours arising in immunocompetent individuals express either latency type I or II gene products, but not the latency-III gene products. Despite the expression of defined "non-self" viral gene products (i.c. proteins associated with latency type-I/-II) these tumours are not eradicated by the host immune system. This may either be a direct consequence of the sub-dominance of latency-I/-II gene products expressed on these tumour cells, only inducing suboptimal or inadequate T-cell immune responses or due to the induction of local T-cell anergy due to the secretion by these tumour cells of immunomodulatory substances, such as IL-10 and (fragments of) LMP1. Alternatively this may be a consequence of the induction and selection of tumour cells with high level of apoptosis resistance, e.g. by upregulation of A20/Bcl-2. Importantly, immunocompetent patients with EBV+ tumours hardly have significant T-cell or antibody responses to latency-associated membrane proteins, although these responses tend to be somewhat higher than in healthy EBV carriers (Meij et al J. Infect. Dis. (1999) 179; 1108-1115 and Frisan et al, Blood (1995) 86; 1493-1501).

Thus, immunocompetent patients with EBV+ tumours are incapable of mounting effective immune responses directed against the "non-self" tumor-associated viral gene products. Tumour-cell induced immunomodulation (suppression) and tumour cell apoptosis resistance may further render local T-cell immune responses ineffective. It is contemplated that antibody reagents recognising EBV specific molecules expressed on the EBV+ tumour cell surface (herein also referred to as EBV-encoded tumour-associated latent membrane proteins or, shortly, as Sty-encoded membrane proteins) should be more effective and would not be influenced by these local immune escape mechanisms. Identification of extracellular domains of such EBV-encoded membrane proteins and the availability of antibody reagents against said domains is therefore a long felt need in the art to develop medicaments against and diagnostics for EBV driven malignant cell growth.

Several EBV-encoded tumour cell-associated membrane proteins are described in the art; however, it has not yet been shown that such membrane proteins comprise extracellular domains, suitable for antibody interaction. As stated above, antibodies against such domains have not yet been described. The existence of defined EBV-encoded tumour cell-associated membrane proteins was first suspected on the basis of functional analyses of T-cell responses against EBV-transformed B-cells and these hypothetical structures were operationally defined as LYDMA (Lymphocyte-determined membrane antigens) (Szigeti et al, Proc. Natl. Acad. Sci. USA. (1984) 81; 4178-4182). Subsequent studies revealed that most of the LYDMA reactivity was rather derived from peptide fragments of the family of nuclear antigens (esp. EBNA3 family) presented in the context of MHC-1 molecules on the cell surface (Burrows et al, J. Exp. Med. (1990) 171; 345-349). Biochemical and molecular analysis and DNA sequencing studies subsequently revealed the existence of at least two types of latency-associated membrane proteins, called LMP1 and LMP2, the latter existing in two forms LMP2A and LMP2B, LMP2B lacking the first 119 amino acids of LMP2A (Rowe, Frontiers in Bioscience (1999) 4; 346-371).

Sequence analysis of the genes encoding LMP1 and LMP2 predicted the existence of several hydrophobic domains within these proteins, suggesting LMP1 to contain 6 membrane spanning domains and LMP2A and 2B to contain 12 such domains. (Rowe, Frontiers in Bioscience (1999) 4; 346-371).

Using monoclonal antibodies reactive with domains in the proposed cytoplasmic regions of LMP1 and LMP2, their association with various membrane compartments within the EBV-infected cell was demonstrated. These studies also revealed LMP1 and LMP2 to co-localise in these membrane compartments, preferentially in so-called glycosphingolipid containing microdomains or rafts (Clausse et al, Virol. (1997) 228; 283-293).

Khanna et al. (J. Exp. Med. 176 (1992); 169-176 and Eur. J. Immunol. 28 (1998); 451-458) describe peptide fragments of LMP1 as possible HLA-associated antigens and ascribe a putative role to the said fragments in the MHC mediated cellular immune response. In the cellular immune response, both self and non-self proteins are expressed and intracellularly cleaved to peptide fragments and are, complexed with HLA, presented on the outer surface of the cell. Such fragments can therefore not be identified as extracellular epitopes triggering a humoral immune response, but merely are functioning as putative HLA-associated epitopes. No suggestion is made by Khanna et al. whether the LMP1 fragments are intracellular, transdomain or extracellular portions of LMP1.

A third latency-associated membrane protein was more recently identified to be encoded in the BARF1 reading frame on the EBV genome, and was originally described as an early gene product (Zhang et al, J. Virol. (1988) 62; 1862-1869). BARF1 is specifically expressed in EBV-associated carcinomas and appears to be not expressed in EBV-associated lymphomas (zur Hausen et al, supra, Brink et al, supra, and European patent application 98200655.3)

The structure of the BARF1 gene is even less well defined. Recent data suggest that BARF1 is anchored in the plasma membrane by a single transmembrane domain in the N-terminus and possibly is secreted from the cell as well (Strockbine et al, J. Virol. (1998) 72; 4015-4021). Human sera which contain reactivity to BARF1 may mediate the elimination of BARF1-expressing cells although the domains relevant for this killing activity have not been defined (Tanner J E, et al. J. Infect. Dis. (1997) 175; 38-46).

In the above characterisation of LMP1, LMP2 and BARF1, it was not contemplated nor proven whether these proteins contained outer extracellular loops actually protruding from the cell membrane, and it was not known whether against such putative loops antibodies could be generated.

SUMMARY OF THE INVENTION

According to an aspect of the present invention, an isolated peptide is provided comprising an extracellular epitope of Epstein-Barr virus (EBV) encoded latent membrane proteins, characterized an that it is accessible on the outer cell surface of EBV-transformed mammalian cells for binding by antibody reagents, the peptide comprising one of the following:
SEQ ID 1 (LMP1, extracellular loop 1);
SEQ ID 2 (LMP1, extracellular loop 2);
SEQ ID 3 (LMP1, extracellular loop 3);
SEQ ID 4 (LMP2, extracellular loop 1);
SEQ ID 5 (LMP2, extracellular loop 2);
SEQ ID 6 (LMP2, extracellular loop 3);
SEQ ID 7 (LMP2, extracellular loop 4);
SEQ ID 8 (LMP2, extracellular loop 5);
SEQ ID 9 (LMP2, extracellular loop 6);
SEQ ID 10 (BARF1, SEQ 40-79);
SEQ ID 11 (BARF1, SEQ 80-154);
SEQ ID 12 (BARF1, SEQ 155-188); or
SEQ ID 13 (BARF1, SEQ 188-221).

According to another aspect of the invention, an isolated peptide is provided characterized in that it is accessible on the outer cell surface of EBV-transformed mammalian cells for binding by antibody reagents, the peptide having at least 80% amino acid sequence identity to:
(a) the amino acid sequence of SEQ ID 1 (LMP1, extracellular loop 1);
(b) the amino acid sequence of SEQ ID 2 (LMP1, extracellular loop 2);
(c) the amino acid sequence of SEQ ID 3 (LMP1, extracellular loop 3);
(d) the amino acid sequence of SEQ ID 4 (LMP2, extracellular loop 1);
(e) the amino acid sequence of SEQ ID 5 (LMP2, extracellular loop 2);
(f) the amino acid sequence of SEQ ID 6 (LMP2, extracellular loop 3);
(g) the amino acid sequence of SEQ ID 7 (LMP2, extracellular loop 4);
(h) the amino acid sequence of SEQ ID 8 (LMP2, extracellular loop 5);
(i) the amino acid sequence of SEQ ID 9 (LMP2, extracellular loop 6);
(j) the amino acid sequence of SEQ ID 10 (BARF1, SEQ 40-79);
(k) the amino acid sequence of SEQ ID 11 (BARF1, SEQ 80-154);
(l) the amino acid sequence of SEQ ID 12 (BARF1, SEQ 155-188); or
(m) the amino acid sequence of SEQ ID 13 (BARF1, SEQ 188-221).

According to yet another aspect of the invention, a method for identifying extracellular epitopes of Epstein Barr virus (EBV) encoded latent membrane proteins is provided comprising the steps of:
A) providing the amino acid sequence of at least one open reading frame (ORF) of the EBV genome;

B) determining at least one putative extracellular domain contained within the amino acid sequence of (A);

C) preparing a peptide comprising the putative extracellular domain of (B) or a part thereof in a constrained forced circular form, the peptide not comprising the full-length ORF;

D) preparing an antibody reagent capable of specifically binding with the peptide of (C);

E) reacting the antibody reagent of (D) with viable EBV transformed mammalian cells; and F) detecting specific binding of the antibody reagent to the cell surface of the EBV transformed mammalian cells.

According to yet another aspect of the present invention, a method for the preparation of monoclonal antibody reagents capable of binding with extracellular epitopes of Epstein Barr virus (EBV) encoded membrane proteins, expressed on the outer cell surface of EBV-transformed mammalian cells is provided, comprising the steps of:

1) providing an expression library, comprising mammalian genetic material, the expression library being a high-diversity library containing at least $10^9$ different clones;

2) contacting with the said library a peptide, comprising the extracellular epitope, the said peptide being identified by a method, comprising the steps of:

A) providing the amino acid sequence of at least one open reading frame (ORF) of the EBV genome;

B) determining at least one putative extracellular domain contained within the amino acid sequence of A);

C) preparation of a peptide comprising the putative extracellular domain of B) or a part thereof, the peptide not comprising the full-length ORF;

D) preparation of an antibody reagent capable of specifically binding with the peptide of C);

E) reacting the antibody reagent of D) with viable EBV transformed mammalian cells;

F) detecting specific binding of the antibody reagent to the cell surface of the EBV transformed mammalian cells;

3) allowing the peptide to specifically bind to organisms of the said library;

4) isolating the organisms whereto the peptide is specifically bound;

5) preparing single clones of the isolated organisms;

6) culturing a clone of step 5) under conditions that the mammalian genetic material is expressed; and 7) isolating the expression product of step 6).

According to another aspect of the present invention, a method for the preparation of monoclonal antibody reagents capable of binding with extracellular epitopes of Epstein Barr virus (EBV) encoded membrane proteins, expressed on the outer cell surface of EBV-transformed mammalian cells is provided, comprising the steps of:

1) providing an expression library, comprising mammalian genetic material, the expression library being a high-diversity library containing at least $10^9$ different clones;

2) contacting with the said library viable EBV-transformed cells expressing on their surface one or more peptide epitopes, identified according to a method, comprising the steps of:

A) providing the amino acid sequence of at least one open reading frame (ORF) of the EBV genome;

B) determining at least one putative extracellular domain contained within the amino acid sequence of A);

C) preparation of a peptide comprising the extracellular domain of B) or a part thereof, the peptide not comprising the full-length ORF;

D) preparation of an antibody reagent capable of specifically binding with the peptide of C);

E) reacting the antibody reagent of D) with viable EBV transformed mammalian cells;

F) detecting specific binding of the antibody reagent to the cell surface of the EBV transformed mammalian cells;

3) allowing the cells to specifically bind to organisms of the said library;

4) isolating the organisms whereto the cells are specifically bound;

5) preparing single clones of the isolated organisms;

6) culturing a clone of step 5) under conditions that the mammalian genetic material is expressed; and 7) isolating the expression product of step 6).

According to yet another aspect of the present invention, a method for the identification of extracellular epitopes of Epstein Barr virus (EBV) encoded membrane proteins, expressed on the outer cell surface of EBV-transformed mammalian cells is provided, comprising the steps of:

A) providing the amino acid sequence of at least one open reading frame (ORE') of the EBV genome;

B) determining at least one putative extracellular domain contained within the amino acid sequence of A);

C) preparation of a peptide comprising the extracellular domain of B) or a part thereof, the peptide not comprising the full-length ORF;

D) preparation of an antibody reagent capable of specifically binding with the peptide of C);

E) reacting the antibody reagent of D) with viable EBV transformed mammalian cells;

F) detecting specific binding of the antibody reagent to the cell surface of the EBV transformed mammalian cells.

According to yet another aspect of the present invention, a method for the selection of antibody reagents capable of binding with extracellular epitopes of Epstein Barr virus (EBV) encoded membrane proteins, expressed on the outer cell surface of EBV-transformed mammalian cells is provided, comprising the steps of:

A) providing the amino acid sequence of at least one open reading frame (ORE) of the EBV genome;

B) determining at least one putative extracellular domain contained within the amino acid sequence of A);

C) preparation of a peptide comprising the extracellular domain of B) or a part thereof, the peptide not comprising the full-length ORF;

D) preparation of an antibody reagent capable of specifically binding with the peptide of C);

E) reacting the antibody reagent of D) with viable EBV transformed mammalian cells;

F) detecting specific binding of the antibody reagent to the cell surface of the EBV transformed mammalian cells; and G) selecting the detected antibody reagent of step F).

These and other aspects, features and advantages of the present invention will be described or become apparent from the following detailed description of preferred embodiments, which is to be read in connection with the accompanying drawings.

BRIEF DESCRIPTION OF THE DRAWINGS

The invention will be further illustrated with the following figures and examples, which are not meant to limit the scope of the invention.

FIGS. 3 E-F show similar analysis with rabbit anti-LMP2 loop2 and loop 5 sera respectively;

FIGS. 3 G-I show the reactivity of the sera of Guinea pigs immunised with different peptides derived from the BARF1 sequence;

A1: MoAb OT22CN anti-LMP1 N-terminus (AA1-13) A2: R-a-LMP1 loop3

B1: Pre-serum B2: K153 anti-LMP2 (SDS-PAGE purified LMP2) B3-4 & B5-6: K154 &K155 as B1-2

B7: anti-LMP2 Loop 5 pre-serum B8: anti-LMP2 loop5 B9-10: Similar for LMP2 loop2.

C4: Pre-serum C5: GP-anti-BARF1-N-term C6: Pre-serum C7: GP-anti-BARF1-middle

C8: Pre-serum C9: GP-anti-BARF1-C-term C10: Rabbit anti-BARF1-GST

Figure 5:
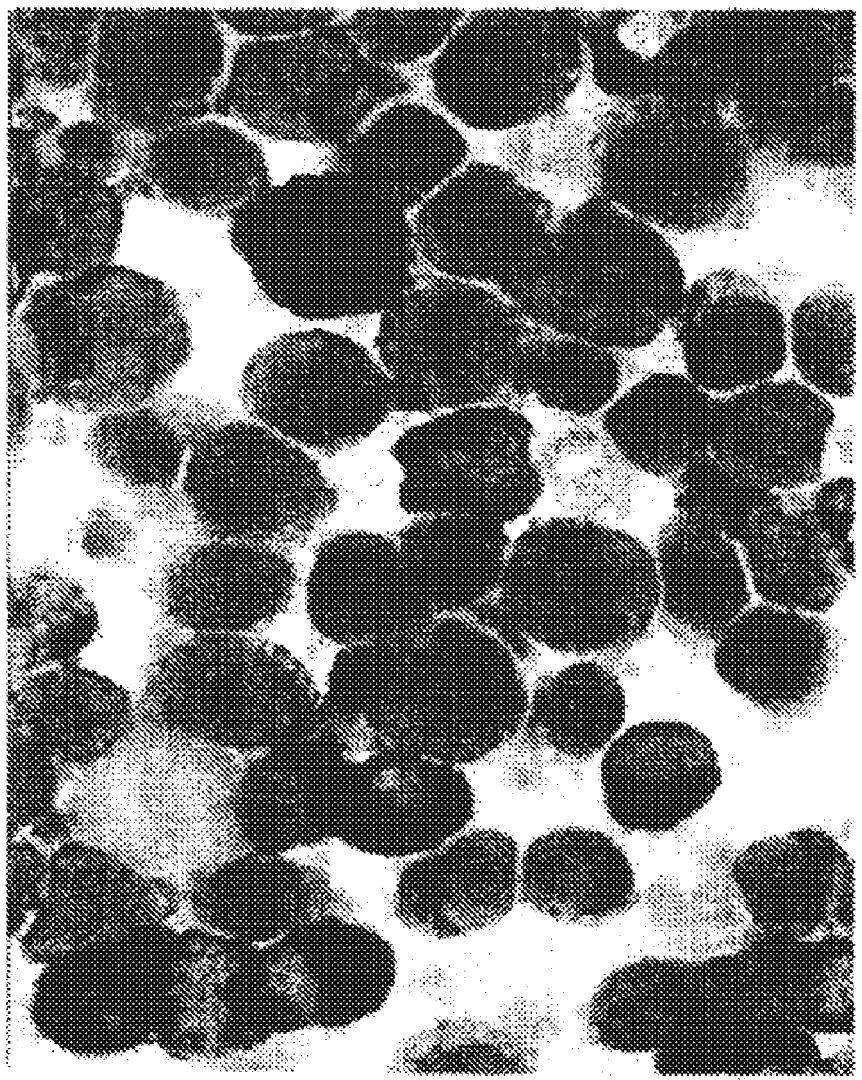
Figure 6:
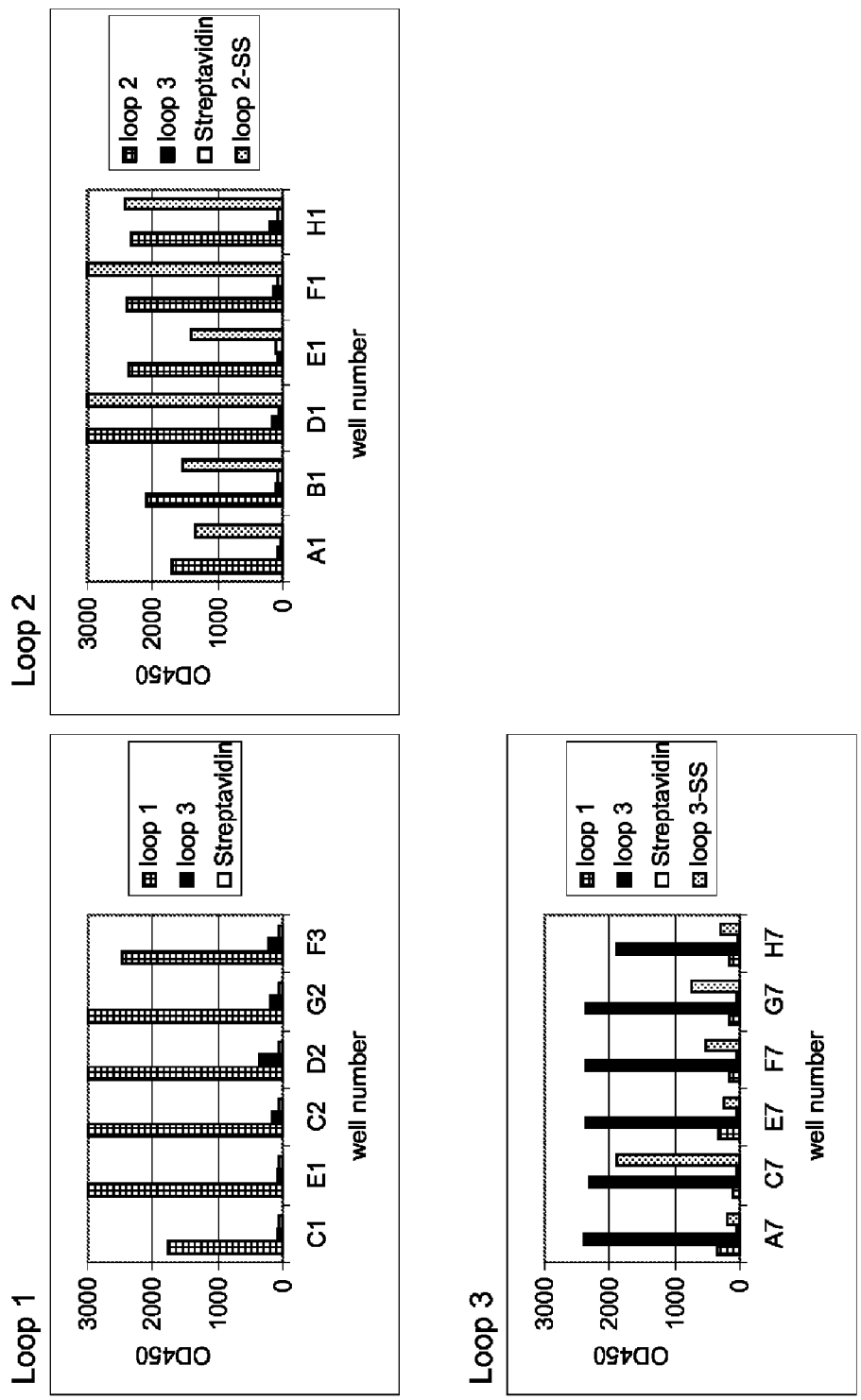
Figure 7:
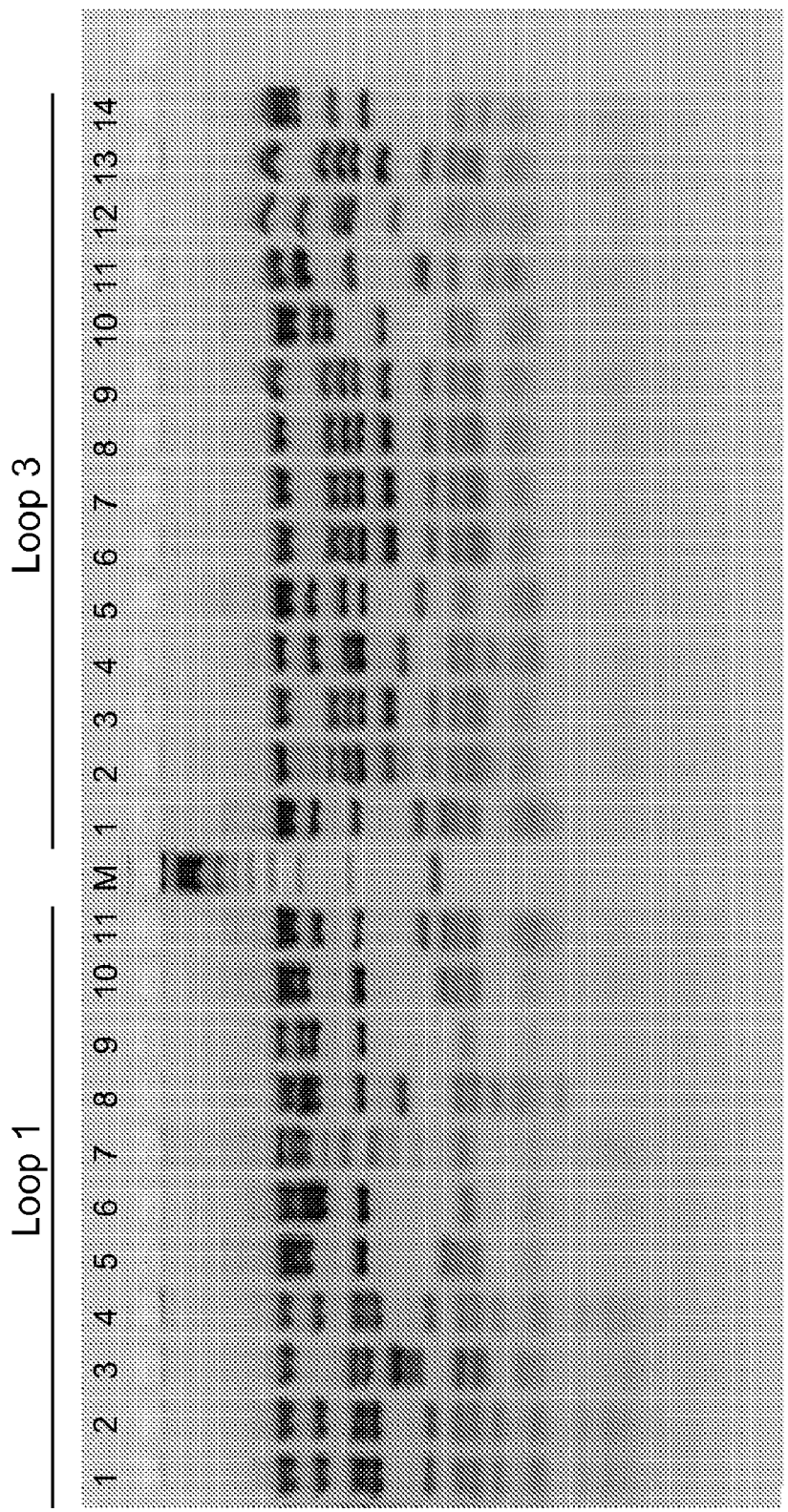
Figure 8:
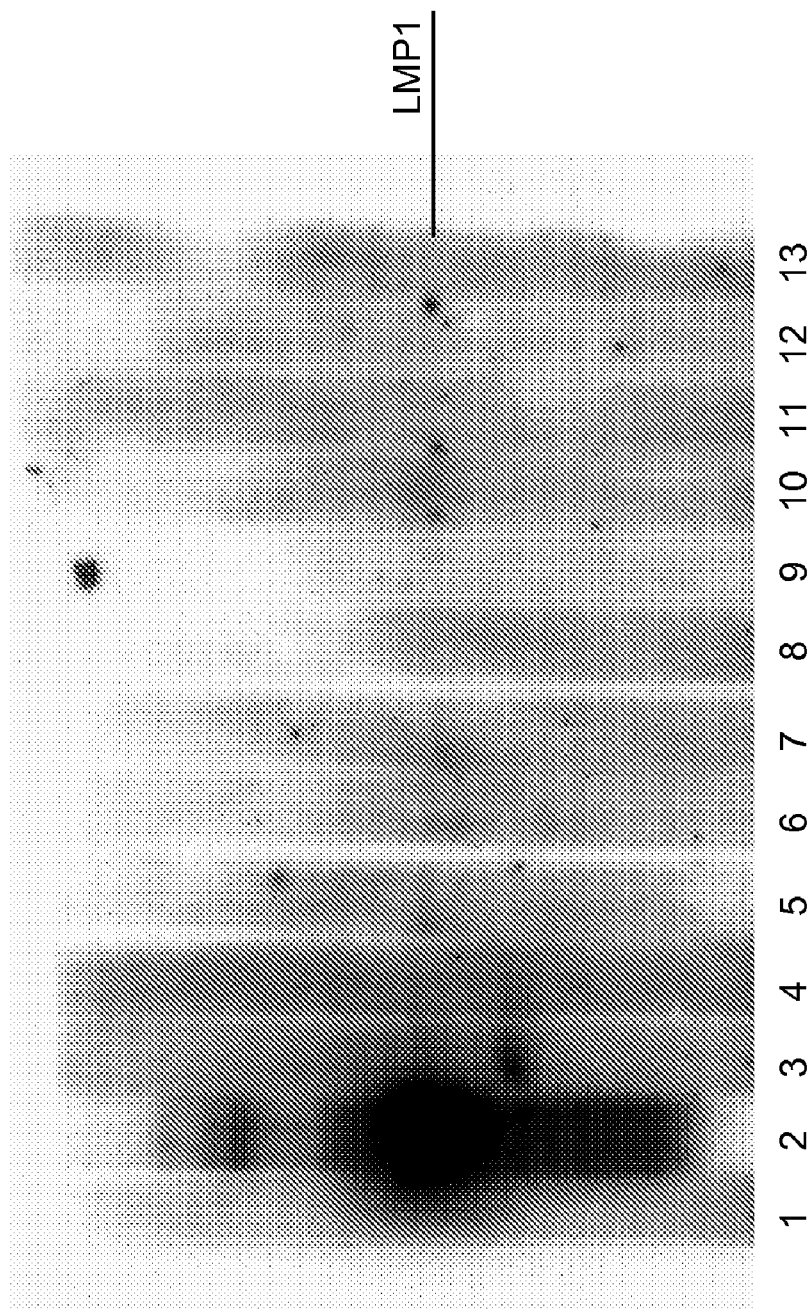

FIG. 5 shows a microscopic view (200×) showing characteristic LMP1-specific staining of acetone-fixed and permeabilised JY-cells using anti-LMP1 antibody reagents;

FIG. 6 shows bar diagrams showing results of peptide ELISA with individual Phage-Ab clones (indicated below each bar), selected with different LMP1-loop-1, -2, -3 specific peptides at round 3 and 4 (see example 3);

FIG. 7 shows results of DNA fingerprint analysis for individual clones picked after the third selection round using LMP1-loop-1 and loop-3 peptides;

FIG. 8 shows an ECL-western blot analysis using purified LMP1 as antigen, testing soluble human phage derived Fab's; Lane 1 and 2 represent negative and positive control reactions respectively, obtained with a non-relevant and an anti-LMP1-specific monoclonal antibody. Lanes 3-13 show that for some soluble phage Fab's (#3, 4, 5, 6, 7, 10) a weak reactive band was detected at the expected size of full length LMP1.

Figure 9:
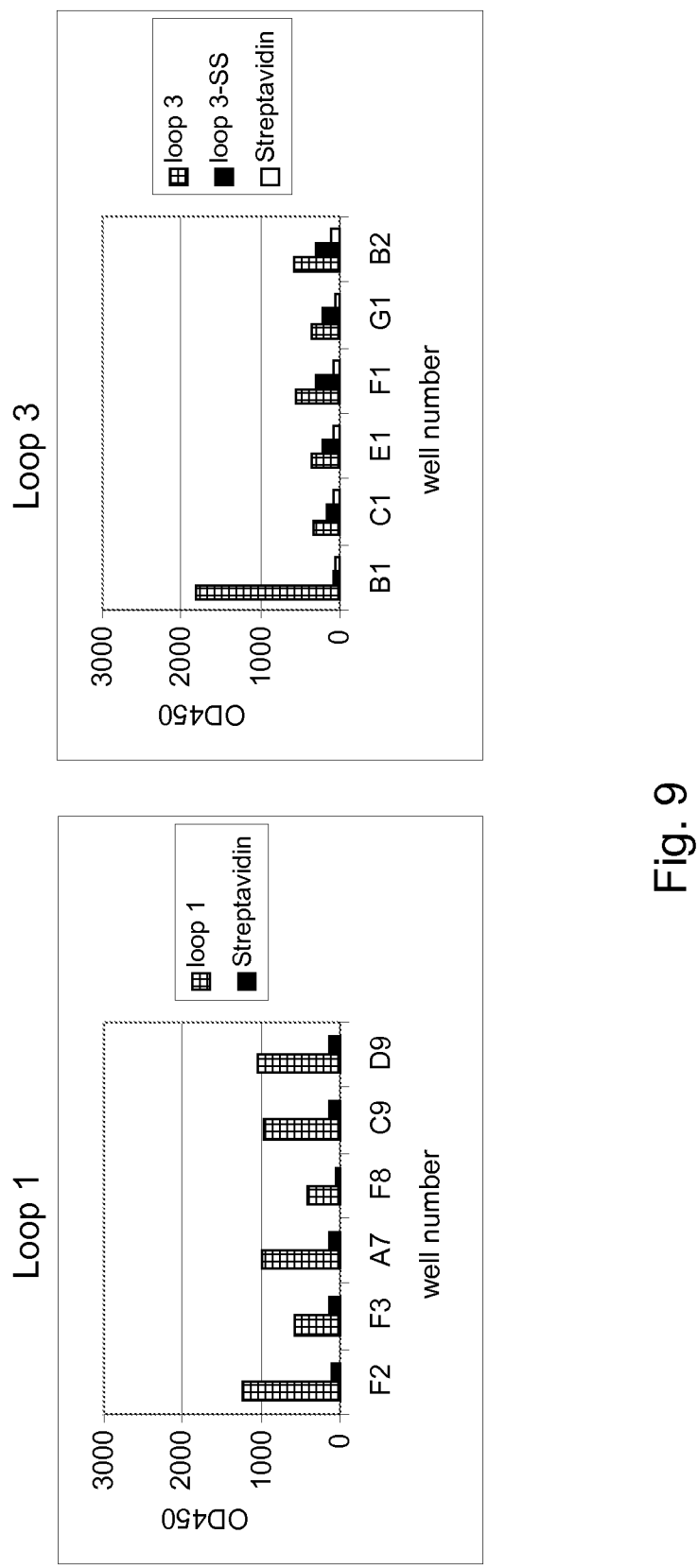

FIG. 9 shows a diagram showing the peptide-ELISA reactivity of induced phage colonies after selection on JY-cells.

DETAILED DESCRIPTION OF PREFERRED EMBODIMENTS

The present invention now for the first time provides a method for the identification of extracellular epitopes of Epstein Barr virus (EBV) encoded membrane proteins, expressed on the cuter cell surface of EBV-transformed mammalian cells, comprising the steps of:
A) providing the amino acid sequence of at least one open reading frame (ORF) of the EBV genome,
B) determining at least one putative extracellular domain contained within the amino acid sequence of A),
C) preparation of a peptide comprising the putative extracellular domain of B) or a part thereof, the peptide not comprising the full-length ORE',
D) preparation of an antibody reagent capable of specifically binding with the peptide of C,
E) reacting the antibody reagent of D) with viable EBV transformed mammalian cells,
F) detecting specific binding of the antibody reagent to the cell surface of the EBV transformed mammalian cells.

The term "extracellular epitopes, expressed on the outer cell surface" herein is defined parts of a protein, that are displayed at the outer cell surface when present in the native protein. Said epitopes are therefore to be considered as extracellular portions of the said protein, and potentially play an important role in triggering a humoral immune response against the said protein, in contrast to protein fragments, that may be displayed at the outer cell surface in association with HLA. The latter protein fragments may, when present in the native protein, be part of intracellular, transmembrane or extracellular portion of the protein, or combinations thereof. Such latter fragments can possibly play a role in the cellular MHC mediated immune response. For an overview of the cellular and humoral immune response pathway, reference is made to Roitt, I. M., Essential Immunology, 9th Edition (1997), Blackwell Science Inc. New York, USA, herein incorporated by reference.

The term "protein" includes single-chain polypeptide molecules as well as multiple-polypeptide complexes where individual constituent polypeptides are linked by covalent or non-covalent means. The term "peptide" includes peptides of two or more amino acids in length, typically having more than 5, 10 or 20 amino acids. An amino sequence of more than 100 amino acids is referred to as "protein".

The amino acid sequences of LMP1, LMP2 and BARF1 have been defined in previous studies and are readily available in the Genbank and Swiss-Prot databases (e.g., LMP1: BAA00948; LMP2a:AAA45884; BARF1:CAA24809).

The ORFs, as well as putative extracellular domains can easily be determined by the skilled person, e.g. by using a suitable computer program, known in the art, as e.g. provided in the GCG Wisconsin package (University of Wisconsin, Genetics Computer Group Inc. U.S.A.; Devereux et al., 1984, Nucleic Acids Research 12:387).

Numerous methods for the preparation of peptides are known in the art; e.g. peptides can be produced using fMoc chemistry using a solid phase peptide synthesiser (e.g. from Applied Biosystems, USA), by enzymatic or chemical cleavage of the native protein, or by genetic engineering techniques. Peptides for use according to the method of the present invention can comprise the complete sequence of the putative extracellular domain or a part thereof, as long as an antibody reagent, specifically binding with the said peptide part can be prepared (see below). Further, the peptide may contain additional sequences, such as additional stretches of amino acids, enabling the peptide to be coupled to a solid matrix (such as resins, used for column chromatography) or may be linked to small additional molecules (such as e.g. biotin) for coupling to a carrier protein (such as streptavidin).

In the art, methods for the preparation of antibody reagents having specific peptide binding capacities are known (See; Current Protocols in Immunology (eds. J. E. Coligan et al.; Publ. J. Wiley & Sons. 1992-2001, herein incorporated by reference). Antibody reagents may be produced following specific immunisation of animals including humans with the protein of interest, by selecting and immortalising naive or specific antibody producing B-cells and by genetic engineering, e.g. by generating expression libraries using the genetic information included in such B-cells i.e. by cloning animal or human repertoires and expressed in micro-organisms or by complete artificial construction of such libraries. However, as a first step, it is preferred to use polyclonal serum of animals, immunised with the peptide of interest for the antibody reagents to be prepared in step D) and to be used in step E) of the method according to the present invention.

"Specifically binding" refers in this case to a specific epitope-antibody idiotype interaction, excluding unspecific protein/protein interaction. The binding of the antibody reagent to the defined amino acid sequence containing Peptides is mediated via the "idiotope" on the antibody. The idiotope is contained as a conformational domain within the variable region of the antibody molecule and is created by the 3-dimensional folding of the so-called complementary determining regions. Binding via the constant or flanking domains that form the antibody backbone structure is not considered specific. The terms epitope and idiotype are known in the art; reference is made to Roitt I. M., supra. Methods for selecting and isolation of specifically bound antibody reagents and for discriminating between specific and unspecific binding are known in the art, and may e.g. involve washing procedures at such conditions that the specific binding is left intact, whereas unspecific binding is cancelled.

The term "antibody reagent" is commonly understood in the art and refers to any molecule, capable of specifically binding to a hapten or epitope. An antibody molecule consists of an antigen binding moiety, usually referred to as the Fv-fragment, a structural part referred to as the constant domain(s) and a part mediating biologic functions, usually referred to as the Fc-part which also comprises several constant domains. The antigen-binding domain of the antibody Fv-fragment consists of several conformationally defined amino acid sequences, called the complementary determining regions (CDR's), which form a three dimensional structure capable of interacting with a distinct antigen molecule, which may be a hapten, oligosaccharide, oligonucleotide, oligopeptide, protein or alternative molecules. Such antigen-binding domains can be expressed in a variety of molecular forms and complexes, while maintaining its antigen-binding properties. Such antibodies, antigen-binding domains or Fv-molecules are herein collectively referred to as "antibody reagents".

By reacting the thus obtained antibody reagent, such as polyclonal serum or a cloned singular antibody or a fragment thereof in vitro with preferably viable EBV transformed cells under conditions that the antibody reagent can specifically bind to epitopes displayed on the outer cell surface of the viable EBV transformed cells, it can be monitored whether the antibody reagent specifically binds to the surface of the EBV transformed cells. In the art, several methods for the determination whether such binding has taken place are known; e.g. in situ staining techniques wherein the EBV transformed cells, having the antibody reagent bound to the outer cell surface thereof, are fixed in suspension or on microscope glass slides. E.g. secondary antibodies, specific for the antibody reagent, and conjugated to a marker that can be visualised can be used to bind to the antibody reagent, bound to the outer cell surface of the EBV transformed cells. Detecting the above binding of the antibody reagent with the EBV transformed cells is an indication that the peptide is an epitope, present on the outer surface of the EBV infected cells, and is thus identified as an extracellular epitope of EBV encoded membrane protein.

The above prepared antibody reagent is thus capable of specifically binding with an epitope on EBV transformed cells. In a second aspect, the present invention therefore relates to a method for the selection of antibody reagents capable of binding with extracellular epitopes of Epstein Barr virus (EBV) encoded membrane proteins, expressed on the outer cell surface of EBV-transformed mammalian cells, comprising the steps of:

A) providing the amino acid sequence of at least one open reading frame (ORF) of the EBV genome,
B) determining at least one putative extracellular domain contained within the amino acid sequence of A),
C) preparation of a peptide comprising the extracellular domain of B) or a part thereof, the peptide not comprising the full-length ORF,
D) preparation of an antibody reagent capable of specifically binding with the peptide of C),
E) reacting the antibody reagent of D) with viable EBV transformed mammalian cells,
F) detecting specific binding of the antibody reagent to the cell surface of the EBV transformed mammalian cells,
G) selecting the detected antibody reagent of F).

Steps A)-F) are the same as describes above for the identification of the epitopes; the antibody reagent, raised against the peptide of interest can be present in a polyclonal mixture of numerous different antibody reagents, the majority of which not being specific for the prepared peptide. Antibody reagents that specifically bind to the EBV encoded epitope can be selected and isolated from an antibody reagent preparation. In the art, methods for the selection and isolation of the antibody reagent of interest from a pool of antibody reagent of different specificity are known.

In a preferred embodiment, monospecific antibody reagents (i.e. antibody reagents that bind to the same epitope, but can be different from one another in e.g. binding strength or in binding to different sites on the epitope) are produced and selected, wherein the above step G) comprises the steps of:

G1) immunising an animal with the peptide of step C),
G2) preparing body fluid of the immunised animal, comprising antibody reagents,
G3) preparing a solid phase affinity matrix comprising the peptide bound to the said matrix,
G4) contacting the body fluid with the matrix,
G5) allowing specific binding of antibody from the body fluid to the peptide bound to the matrix,
G6) isolation of the antibody reagents specifically bound to the peptides.

Immunisation of the animal can be performed by injecting the peptide of interest into an animal, preferably a mammal, including humans, as explained above. When the antibody reagent in step D) is prepared by such immunisation, steps G1) and G2) can together be the same as step D). The immunisation will result in a polyclonal serum, which comprises at least one specific antibody for the peptide of interest (i.e. the above described epitope).

If e.g. the antibody reagent is produced as polyclonal serum from an animal, such as a rabbit or guinea pig or even a human, B cells of the immunised animal can be isolated and be used for the preparation of monoclonal antibodies by the hybridoma technique or modifications thereof (Kohler and Milstein, Nature 256 (1975):495-497; van Meel et al., J. Immunol. Meth. 80 (1985):267-276; Steenbakkers et al, Human Antibodies and Hybridomas 4 (1993):166-173; Schmidt et al., J. Immunol. Meth. 255 (2001) 93-102). Thus, in another attractive embodiment of the present invention, monoclonal antibodies are produced and selected, wherein the above step G) comprises the steps of:

G1) immunising an animal with the peptide of step C),
G2) providing B cells producing antibody reagents from the immunised animal of G1),
G3) preparing a solid phase affinity matrix comprising the peptide bound to the said matrix,
G4) contacting the B cells of G2) with the matrix, G5) allowing specific binding of the B cells to the peptide bound to the matrix, G6) isolation of the B cells, specifically bound to the peptides.

The immunization of the animal, preferably a mammal, including humans, in step G1) will result in B-cells producing antibodies that specifically bind to the said peptide, which B cells can be obtained from the circulation or defined lymphoid organs from the immunized animal, i.c spleen, lymph nodes or bone marrow. Methods for binding B cells to a suitable matrix and isolation thereof are known in the art. The isolated B cells can be used for monoclonal antibody production using the hybridoma fusion techniques referred to above.

In a subsequent step, the said peptide is bound to a solid phase matrix, such as e.g. resins, used for column chromatography, or solid beads, such as magnetic beads in the art, method for binding peptides to a solid matrix are known. The skilled person is also aware of suitable matrices, available in the art. For proper binding, the peptide may comprise additional amino acids, such as a stretch of lysine residues, or spacer arms at the termini thereof facilitating the binding of the peptide to the matrix.

The polyclonal antibodies can be obtained in a body fluid of the immunised animal, such as e.g. ascites fluid, whole blood or blood serum.

In a following step, the body fluid is contacted with the matrix of step G2) at such conditions that the antibodies can bind to the peptides, bound to the said matrix. The term "body fluid" is also meant to encompass any liquid medium, comprising the polyclonal antibodies from the said body liquid, e.g. obtained by a purification step. The antibodies, capable of specifically binding to the peptide on the matrix will bind thereto; any possible unspecific binding can be eliminated by choosing the proper binding conditions, or by subjecting the matrix to which the antibodies are bound to a washing procedure, wherein the unspecific antibodies are washed away, the specific antibodies remaining bound to the peptides. The skilled person will be capable of determining the proper binding and washing conditions.

The antibody reagent, specifically bound to the peptides, can conveniently be isolated by e.g. washing procedures as indicated above, and/or by retrieving the solid matrix from the binding or washing medium. In case the matrix is comprises magnetic beads, the matrix-bound specific antibodies can be isolated by magnetic forces; in a second step, the binding between the antibodies and the peptides can be removed, yielding the specific antibodies in isolated form. In case the matrix comprises a resin, packed in a chromatography column, the unspecific antibodies and other components are in a first step washed from the column; subsequently the antibodies can be isolated by elution from the column.

Preferably, the ORFs provided according to the method of the invention are chosen from the above-discussed EBV encoded membrane proteins LMP1, LMP2 and BARF1, the amino acid sequences thereof being known in the art and published (Genbank Accession numbers LMP1:BAA00948; LMP2a:AAA45884; BARF1:CAA24809, incorporated by reference herein). Most preferably, the putative extracellular domains are chosen from the amino acid sequences, chosen from the group, consisting of:

SEQ ID 1 (LMP1, extracellular loop 1),
SEQ ID 2 (LMP1, extracellular loop 2),
SEQ ID 3 (LMP1, extracellular loop 3),
SEQ ID 4 (LMP2, extracellular loop 1),
SEQ ID 5 (LMP2, extracellular loop 2),
SEQ ID 6 (LMP2, extracellular loop 3),
SEQ ID 7 (LMP2, extracellular loop 4),
SEQ ID 8 (LMP2, extracellular loop 5),
SEQ ID 9 (LMP2, extracellular loop 6),
SEQ ID 10 (BARF1, SEQ 40-79),
SEQ ID 11 (BARF1, SEQ 80-154),
SEQ ID 12 (BARF1, SEQ 155-188) and
SEQ ID 13 (BARF1, SEQ 188-221).

It was found that by using the above sequences, antibody reagents could be selected and isolated, specific for the said peptides, the said peptides being expressed on the outer cell surface of EBV-transformed mammalian cells (see examples 1-3). Thus, the said peptides could be identified as extracellular EBV encoded epitopes, and antibody reagents could be generated that were specific for the said epitopes. E.G. polyclonal antibodies could be generated by the immunisation of rabbits with synthetic peptides, the amino acid sequence of which were based on parts of the known amino acid sequences of LMP1 and LMP2, located between the hydrophobic, putatively membrane spanning domains of said proteins (i.e. peptides comprising any of the SEQ ID Nos 1-9). Further, synthetic peptides, comprising parts of the putative single transmembrane domain of BARF1 could be used (i.e. peptides comprising any of the SEQ ID Nos 10-13).

In a very preferred embodiment, the peptide of step C) of the above methods of the invention comprises two cystein residues, where between the putative extracellular domain or part thereof is located, the said cystein residues being oxidised forming a S—S bond between the said cystein residues. Such a peptide comprises the extracellular domain in a constrained "forced circular" form, therewith mimicking the natural conformation of the domain, when part of the natural protein in the cell membrane. It could be shown that the peptides in constrained conformation resulted in improved specific binding of antibody reagents and thus to improved selection and isolation of the antibody reagents (see e.g. examples 2-4). The peptides can also comprise additional modifications, as e.g. discussed above for the improved binding to a matrix.

In addition to the above embodiment of the invention wherein monospecific and monoclonal antibody reagents are selected and isolated, a special and very advantageous embodiment of the invention provides monoclonal antibody reagents specific for extracellular epitopes of EBV encoded membrane proteins, produced by using expression libraries. Thereto, the invention provides a method for the preparation of monoclonal antibody reagents capable of binding with extracellular epitopes of Epstein Barr virus (EBV) encoded membrane proteins, expressed on the outer cell surface of EBV-transformed mammalian cells, comprising the steps of:

1) providing an expression library, comprising mammalian genetic material,
2) contacting the peptide, identified according to claim 1 with the said library,
3) allowing the peptide to bind to organisms of the said library,
4) isolating the organisms whereto the peptide is specifically bound,
5) preparing single clones of the isolated organisms,
6) culturing a clone of 5) under conditions that the mammalian genetic material is expressed,
7) isolating the expression product of step 6).

In the art, methods for the preparation of suitable expression libraries are known. Expression libraries are defined a set of prokaryotic or eukaryotic cells or organisms, and viruses infecting said cells or organisms, which have been altered by means of genetic engineering to express heterologous protein sequences such as antibodies. E.g., the construction of human antibody libraries and selection of reactive antibody reagents by phage-display techniques and the expression of recombinant human antibodies and antibody fragments has been described in several publications [McCafferty et al., Nature (1990), 348: 552; Griffiths et al., EMBO J. (1994) 13:3245; Marks et al., J. Mol. Biol. (1991) 222: 581; de Boer et al., Hum. Antibod. Hybridomas (1994) 5, 57-64; Vaughan et al., Nature Biotech. (1996) 14:309; and de Haard et al., J. Biol. Chem. (1999) 274: 18218. "Mammalian genetic material" is to be understood herein as a stretch of at least 50, preferably at least 100 nucleotides having at least 60%, preferably at least 80%, most preferably 95-100% sequence homology to mammalian DNA or RNA sequences. Thus, the said material can e.g. be of synthetic origin as well as derived from natural sources.

By contacting the peptide of interest, i.e. comprising an extracellular domain as identified according to the above method of the invention, with the expression library, binding of the peptide with specific clones within the library expressing antibody reagents on their surface is achieved. Thereto, the peptide may be bound to a solid phase or is preferably provided with a selectable moiety, such as a biotin moiety, allowing isolation of the clones bound to the peptides, from the library, by using e.g. streptavidin resins or streptavidin-magnetic beads. However any suitable techniques, known in the art for isolating the clones from the library can be used. (Steenbakkers et al., Human Antibodies and Hybridomas 4 (1993):166-173; Sawyer et al., J. immunol. Meth. 204 (1997) 193-203; Hoogenboom H R, Tibtech 15 (1997) 62-70; de Haard et al. Clin Diagn Lab Immunol. 1998 Sep.; 5(5):636-44; Hanes and Pluckthun, Curr Top Microbiol Immunol. 243 (1999):107-22; Hoogenboom and Chames, Immunol. Today 21 (2000) 371-378). Preferably, the thus isolated clones are checked for binding capacity to the protein, where from the peptide is derived, and/or for binding capacity with the outer cell surface of EBV-transformed cells, as described above. Repeated rounds of peptide-binding and selection may be needed to achieve enrichment of a family of clones with desired peptide-binding activity. Hoogenboom et al., Adv. Drug Deliv. Rev. 31 (1998) 5-31.

In a special embodiment, the peptides are presented in the constrained form, as discussed above.

Single clones can be prepared by techniques, known in the art. An attractive technique therefor is by limiting dilution cloning: following the selection of (populations of) binding clones the individual clones within the population can be selected by limiting dilution culture on host cells allowing the isolation of single antibody-expressing populations. Such individual clones can be assessed for their epitope-binding characteristics, in case their binding to extracellular domains of LMP1, LMP2 and BARF1, as represented either by (constraint) peptides or by intact protein epitopes displayed on EBV-transformed cells. The skilled person will be aware of suitable clone isolation techniques.

The thus prepared clones can be cultured under conditions that the mammalian genetic material, i.e the gene(s) encoding the specific antibody reagent, is expressed. Said culturing conditions are known in the art. [See for instance: Bothman and Pluckthun, Nature Biotech. 16 (1998) 376-380; Shusta et al., Nature Biotech. 16 (1998) 773-777; Liang et al. J. Immunol. Meth. 247 (2001) 119-130]. The antibody reagent can be obtained by isolation thereof, i.e. the expression product of the isolated clone(s), and further purified if desired, according to methods known in the art [See e.g. Current Protocols in immunology (eds. J. E. Coligan et al., Publ. J. Wiley & Sons. 1992-2001].

Preferably, the expression library used in the above method is a high-diversity library containing at least $10^9$, preferably at least $10^{12}$ and most preferably about $10^{15}$ different clones. Suitable high diversity libraries are available in the art; e.g. the single chain antibody phage library as described by Vaughan et al. Nature Biotech. 14 (1996) 309-314 or the human Fab fragment library as described by de Haard et al. J. Biol. Chem. 274 (1999) 18218-18230.

By using polyclonal and monoclonal antibodies, produced using high diversity expression libraries (see e.g. Hoogenboom and Chames, Immunology Today (2000), vol. 21, no. 8, pp 371-378 for a review), it could be demonstrated that LMP1, LMP2 and BARF1 comprise extracellular domains that are exposed and accessible at the cell surface of EBV transformed cells for antibody reagents and may therefore be a target for specific therapeutic approaches (SEE EXAMPLE 3). As illustrated in example 3, a first selection experiment using an antibody library of limited diversity, mainly yielded phage clones reactive with the s-s constraint linker structure common to the selecting peptides and no specific clones could be selected with limited reactivity to a single selecting LMP1, LMP2 or BARF1 peptide structure.

In a very attractive embodiment for the preparation of monoclonal antibody reagents according to the invention, the peptide is an epitope, expressed on the outer surface of viable EBV transformed cells. Thus, instead of an isolated peptide, viable EBV transformed cells, expressing on their outer surface one or more epitopes, identified according to the invention can be used. Thereto, the invention relates to a method for the preparation of monoclonal antibody reagents capable of binding with extracellular epitopes of Epstein Barr virus (EBV) encoded membrane proteins, expressed on the outer cell surface of EBV-transformed mammalian cells, comprising the steps of:

1) providing an expression library, comprising mammalian genetic material,
2) contacting viable EBV-transformed cells expressing on their surface one or more peptide epitopes, identified according to the invention, with the said library,
3) allowing the cells to bind to organisms of the said library,
4) isolating the organisms whereto the cells are specifically bound,
5) preparing single clones of the isolated organisms,
6) culturing a clone of 5) under conditions that the mammalian genetic material is expressed,
7) isolating the expression product of step 6).

In this approach antibody phage libraries are contacted with viable EBV-transformed B-cells. Bound phages are eluted and can further be selected to be non-reactive with control EBV-negative B-cells. Surprisingly such phages are capable of reacting with constraint peptides, but also, however to a lesser extent, with the linear peptides. Immunoblot analysis of soluble Fab's obtained from some of these selected clones revealed a detectable immunoreactive signal with denatured full length protein. This approach is illustrated by Example 4.

In a further aspect, the invention relates to the use of a high-diversity library containing at least $10^9$, preferably at least $10^{12}$ and most preferably about $10^{15}$ different clones for the preparation of monoclonal antibody reagents capable of binding with extracellular epitopes of Epstein Barr virus (EBV) encoded membrane proteins, expressed on the outer cell surface of EBV-transformed mammalian cells. Surprisingly, using a human Fab phage library with extended diversity, such as described by de Haard et al (1999) or de Boer et al (1994), supra, multiple phage clones were obtained that reacted with individual selecting peptides, either in constraint or linear form and which also reacted with the intact protein containing the selecting epitopes (see example 3).

The invention also provides antibody reagents, obtainable according to any of the above-discussed methods according to the present invention, capable of binding with extracellular epitopes of Epstein Barr virus (EBV) encoded membrane proteins, expressed on the cell surface of EBV-transformed mammalian cells.

The present invention also relates to an antibody reagent capable of specifically binding to an amino acid sequence, chosen from the group, consisting of SEQ ID nos. 1-13 and to an amino acid sequence, having at least 80% preferably 90%, most preferably 95% or more homology with one of the amino acid sequences of SEQ ID nos. 1-13. Thus, the present invention also covers antibody reagents, specifically binding to variants, homologues or derivatives of any of the peptides having SEQ ID nos. 1-13 of the present invention, and covers variants, homologues or derivatives of the nucleotide sequence coding for the said peptides.

The terms "variant" or "derivative" in relation to the amino acid sequences of the present invention includes any substitution of, variation of, modification of, replacement of, deletion of or addition of one (or more) amino acids from or to the sequence providing the antibody reagent according to the present invention is capable of specificity binding resultant amino acid sequence preferably having at least the same binding specificity therewith as with the polypeptides presented in the sequence listings. Such variants and derivatives are encompassed by the present invention.

Antibody reagents directed against extracellular domains of proteins incorporated in a cell's membrane, but distinctly extruding from the cell surface, have been shown to bind to the target cells surface and mediate a variety of biological properties. (Glennie M J and Johnson P W M. Immunol. Today (2000) 21; 403-410).

Upon binding, such antibody reagents may induce aggregation and internalisation or release of membrane proteins from the cell surface. Alternatively, antibody reagents bound to the cell surface may bind and activate components of the complement cascade, causing lysis of the targets cells. Similarly, cell-surface bound antibody reagents may bind to Fc-receptors on "killer"-lymphocytes and subsequently activate the elimination process leading to lysis of the target cell. Furthermore, antibody reagents equipped with toxin molecules, radioactive substances or alternative biologic response modifiers, may introduce specific alterations to the target cells. Additionally, antibody reagents may be incorporated in cell-surface molecules of cytotoxic T-cells and "killer" cells thereby redirecting such cytotoxic killer cells to the target cell. Finally antibody reagents equipped with radioactive labels or alternative tracer molecules may be employed in detecting and visualising the target cells for diagnostic purposes.

The antibody reagents according to the present invention are specifically suited for binding to EBV+ (tumour) cells in the circulation, in human (tumour) tissue in vivo and in other biological samples potentially containing EBV-infected cells in vitro and in vivo.

The antibody reagents according to the present invention are specifically suited for the detection of positive (EBV+) tumour cells in peripheral blood, in human (tumour) tissue samples and thin sections thereof and for targeting gene-therapy vectors, "killer" lymphocytes, radiolabels, toxins and additional biological modifiers to EBV+ tumour cells in patients and in biological samples potentially containing EBV-infected (tumour) cells.

The term 'antibody reagents' has been defined above. According to the invention, antibodies may as well comprise mutations, such as deletion, addition and substitution mutations, as long as such a mutated antibody reagent is still capable of specifically binding to one of the above-mentioned amino acid sequences. The antibody reagents can de used for binding EBV-infected cells both in vivo and in vitro.

Thus, by the invention extracellular domains of the EBV-encoded membrane proteins LMP1, LMP2 and BARF1 as epitopes for triggering the humoral immune response can be identified, and peptides comprising said domains and antibody reagents against said extracellular domains can be produced.

The present invention relates in a following aspect to an isolated peptide, capable of being bound by an antibody reagent identified according to the present invention. By definition, such peptides comprise at least one epitope that interacts with the said antibody reagent. Preferably the peptides are chosen from the group, consisting of SEQ ID 1 (LMP1, extracellular loop 1)
SEQ ID 2 (LMP1, extracellular loop 2)
SEQ ID 3 (LMP1, extracellular loop 3)
SEQ ID 4 (LMP2, extracellular loop 1)
SEQ ID 5 (LMP2, extracellular loop 2)
SEQ ID 6 (LMP2, extracellular loop 3)
SEQ ID 7 (LMP2, extracellular loop 4)
SEQ ID 8 (LMP2, extracellular loop. 5)
SEQ ID 9 (LMP2, extracellular loop 6)
SEQ ID 10 (BARF1, SEQ 40-79)
SEQ ID 11 (BARF1, SEQ 80-154)
SEQ ID 12 (BARF1, SEQ 155-188)
SEQ ID 13 (BARF1, SEQ 188-221)

These peptides according to the invention constitute extracellular domains of LMP1, LMP2 and BARF1 respectively, which is demonstrated in example 1. The numbering of the amino acid sequence of the above LMP1, LMP2 and BARF1 are the same as the numbering, used in the SWISS PROT or GENBANK DATABASE.

In a preferred embodiment, the invention relates to an isolated peptide or protein comprising an amino acid sequence, chosen from the group, consisting of SEQ ID nos. 1-13, not being the full length LMP1, LMP2 or BARF1 sequence, nor being 90% or more homologous thereto. This means that the amino acid sequence, encoded by any of the SEQ ID numbers 1-13 may e.g. be incorporated in a non-natural environment, e.g. flanked by amino acid sequences, not or only partially flanking the said sequence in the natural LMP1, LMP2 or BARF1. For example, a hybrid protein wherein any of the extracellular domains of LMP1, LMP2 or BARF1 are present is encompassed by the invention. Such hybrid proteins can e.g. be used as carrier proteins, that can be used as immunogene for active vaccination and immune therapy (see e.g. example 2). Considering the fact that LMP1, LMP2 and BARF1 and their derived submolecular peptide domains are hardly immunogenic in the natural context of EBV-infection in the human host (see e.g. Meij et al; supra), coupling LMP1, LMP2 and/or BARF1 sequences to a carrier sequence is an effective tool for specific immunization and presentation of LMP1, LMP2 and BARF1 sequences to the immune system and will stimulate and improve the induction of specific immune responses to LMP1, LMP2 and BARF1. Procedures for coupling of a protein, a fragment thereof or defined peptide sequences of low endogenous immunogenicity to carrier proteins, such as Keyhole Limpet, Hemocyanine, Tetanus Toxoid and/or mixing with adjuvant formulations such as Freunds, BCG or Alum (etc.) for improving their immunogenicity are well known in the art.

Preferably, the peptide or protein of the invention comprises less than 100 amino acids.

Preferably, the peptide or protein molecules of the invention comprise a sequence with fewer amino acids than the full length amino acid sequence of the LMP1, LMP2 and BARF1 proteins, but containing one or more of the Seq. ID's 1-3, 4-9 and 10-13 respectively. In particular, for LMP1, sequence devoid of the immunosuppressive domain LALLFWL (SEQ ID NO: 18) present in the first transmembrane helix are preferred (Dukers et al, J. Immunol. (2000) 165; 663-670).

The invention also relates to a peptide or protein, comprising an amino acid sequence having at least 80%, preferably at least 90%, most preferably at least 95% homology with any of the amino acid sequences of SEQ ID nos. 1-13, not being the full length LMP1, LMP2 or BARF1 sequence, nor being 90% or more homologous thereto. Such homologous peptides or proteins encode for variants or derivatives of the amino acid sequences of the present invention.

It will be understood that amino acid sequences for use in the invention also include homologous sequences obtained from any source, for example related viral/bacterial proteins, cellular homologues and synthetic peptides, as well as variants or derivatives thereof.

In the context of the present invention, a homologous sequence is taken to include an amino acid sequence which is at least 80 preferably 90% identical, most preferably at least 95 or 98% identical at the amino acid level over at least 5, preferably 8, more preferably 10 amino acids with one of the amino acid sequences as shown in the sequence listing herein. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% Homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package, supra. The default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package, supra. Examples of other software than can perform sequence comparisons include, but are not limited to, the BLAST package (see http://www.ncbi.nih.gov/BLAST/), FASTA (Atschul et al., 1990, J. Mol. Biol., 403-410; FASTA is available for online searching at, for example, http://www.2.ebi.ac.uk.fasta3) and the GENEWORKS suite of comparison tools. However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The amino acid sequence of the extracellular domains of LMP1, LMP2 or BARF1 may be modified for use in the present invention. Typically, modifications are made that maintain the binding specificity of the sequence. Amino acid substitutions may be made, for example from 1, 2 or 3 to 10 substitutions provided that the modified sequence retains the binding specificity with the antibody reagens according to the invention. Amino acid substitutions may include the use of non-naturally occurring analogues, such as homologues with conserved characteristics (see table below), or D-amino acids, or side-chain modified amino acids, synthetically modified amino acids, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Peptides for use in the invention are typically made by recombinant means, for example as described in Maniatis et al., supra. However they may also be made by synthetic means using techniques well known to skilled persons such as solid phase synthesis. Peptides of the invention may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the peptide sequence of interest to allow removal of fusion protein sequences. Preferably the fusion protein will not hinder the binding specificity of the peptide of interest sequence.

Peptides, and the antibody reagents of the invention may be in a substantially isolated form. It will be understood that the peptide/antibody reagent may be mixed with carriers or diluents which will not interfere with the intended purpose thereof and still be regarded as substantially isolated. A peptide or antibody reagent of the invention may also be in a substantially purified form, in which case it will generally comprise said peptide or antibody reagent in a preparation in which more than 90%, e.g. 95%, 98% or 99% thereof in the preparation is a peptide or antibody reagent of the invention.

The invention also relates to a purified nucleic acid sequence, comprising a nucleic acid sequence coding for an amino acid sequence, chosen from the group consisting of SEQ ID nos. 1-13, not encoding the full length LMP1, LMP2 or BARF1 sequence, nor being 90% or more homologous thereto.

The skilled person can easily produce such a nucleic acid sequence when he knows the amino acid sequence. The nucleic acids can be used to easily produce both in vivo and in vitro the amino acid sequences of the extracellular domains of LMP1, LMP2 and BARF1, in order to produce antibody reagents both in vivo and in vitro.

Polynucleotides of the invention comprise nucleic acid sequences encoding the sequences of the invention. It will be understood by a skilled person chat numerous different polynucleotides can encode the same polypeptide as a result of the degeneracy of the genetic code. In addition, it is to be understood that skilled persons may, using routine techniques, make nucleotide substitutions that do not affect the peptide sequence encoded by the polynucleotides of the invention to reflect the codon usage of any particular host organism in which the peptides of the invention are to be expressed.

Polynucleotides of the invention may comprise DNA or RNA, preferably DNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

The nucleotide sequences according to the invention also comprise variants, homologues and derivatives thereof; these are defined as a nucleic acid sequence being at least 80%, preferably at least 90%, most preferably at least 95% homologous to the nucleic acid sequence coding for a peptide having any of the SEQ ID nos. 1-13, or for a variant or derivative peptide thereof being at least 80%, preferably 90%, most preferably 95% homologous thereto.

The terms "variant", "homologue" or "derivative" in relation to the nucleotide sequence of the present invention include any substitution of, variation of, modification of, replacement of, deletion of or addition of one (or more) nucleic acid from or to the sequence providing the resultant nucleotide sequence codes for a peptide with which the antibody reagent according to the invention is capable to specifically bind, preferably having at least the same binding specificity with the said antibody reagents as the sequences presented in the sequence listings.

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Preferably, the nucleic acid sequences (polynucleotides) of the invention are incorporated into a recombinant replicable vector.

The term 'vector' is well known in the art. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example CHO cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Particularly preferred are tissue-specific promoters specific for epithelial cells, for example the human keratin promotor sequence which specifically regulate and induce the expression of different keratin subspecies in differentiating epithelial cells (Caldwell et al, J. Virol. (2000) 74; 1101-1113), and promoters, specific for lymphoid cells, in particular B-lymphocytes, for example the immunoglobulin heavy chain (e.g. Ep.) promotor sequence, which specifically regulate and induce immunoglobulin heavy chain expression in differentiating B-lymphocytes (Longan and Longecker J. Gen. Virol. (2000) 81; 2245-2252). They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Using a vector according to the invention, the nucleic acid sequence encoding one of the above-mentioned extracellular domains can be brought into a biological host cell, of prokaryotic or eukaryotic origin. The said nucleic acid sequence can be either incorporated into the genome of the host, or be present at extrachromosomal elements.

Vectors and polynucleotides of the invention may be introduced into host cells for the purpose of replicating the vectors/polynucleotides and/or expressing the peptides of the invention encoded by the polynucleotides of the invention. Although the peptides of the invention may be produced using prokaryotic cells as host cells, it is preferred to use eukaryotic cells, for example yeast, insect or mammalian cells, in particular mammalian, especially human cells.

Vectors/polynucleotides of the invention may be introduced into suitable host cells using a variety of techniques known in the art, such as transfection, transformation and electroporation. Where vectors/polynucleotides of the invention are to be administered to animals, several techniques are known in the art, for example infection with recombinant viral vectors. such as retroviruses, herpes simplex viruses and adenoviruses, direct injection of nucleic acids and biologic transformation. Such a host cell may express the amino acid sequence, encoding an extracellular domain of LMP1, LMP2 or BARF1, or a part thereof, therewith producing sufficient amounts of the said domains or proteins/peptides comprising the said domain for e.g. preparation of immunogenes for active vaccination and immune therapy, or for the production of antibody reagents according to the present invention (see below). E.g. see Gurunathan et al, Ann. rev. Immunol. (2000) 18; 927-974.

Host cells may be cultured under suitable conditions which allow expression of the peptides of the invention. Expression of the peptides of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Peptides of the invention can be extracted from host cells by a variety of techniques known in the art, including enzymatic, chemical and/or osmotic lysis and physical disruption.

Further, the invention relates to cells, preferably mammalian cells, more preferably human cells, transformed with a vector according to the invention. The term 'transformation' refers to any method of bringing foreign genetic material into a host cell. Using prokaryotic host cells, the term 'transformation' is commonly used in the art. However, this term also encompasses 'transfection', the term commonly used for bringing foreign genetic material into eukaryotic, in particular mammalian cells. Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition. It is however to be understood that the terms "transformation" and "transformed" also refer to the process of infection of a (mammalian) cell by a virus, such as EBV.

In a special embodiment, the invention relates to a method for the production of targeting cells, targeted to cells expressing LMP1, LMP2 or BARF1 comprising the steps of:
  transfecting the cells with genetic information for the antibody reagent according to the invention;
  expressing said antibody reagent on the surface of the said targeting cells.

Such targeting cells will be able to bind cells expressing LMP1, LMP2 and/or BARF1. The targeting cell can e.g. be derived from primary T-, NK (natural killer)-lymphocytes (a Fc-recepter bearing killer cell or a macrophage) to increase or modify their target cell binding specificity without loss of specific receptor signalling function. By incorporating genetic information derived from the antibody reagent into the said cells, and translation thereof and incorporation of the translated products into cell surface structures, such modified T-/NK-cells may be capable of improved recognition, binding and specific elimination of otherwise weakly or non-recognised tumour cells (examples: R. J. Bolhuis and J. W. Gratama, Gene Therapy (1998) δ: 1153, Willemsen et al, Gene Therapy (2000) 7: 1369; Calogero et al, J. Immunotherapy (2000) 23:393).

Upon binding to an EBV infected cell expressing LMP1, LMP2 and/of BARF1, the targeting cell inactivates the infected cell by triggering e.g. a lytic cascade therewith specifically lysing the EBV infected cell.

In another attractive embodiment, the invention relates to a method for the production of targeting viral particles, targeted to cells expressing LMP1, LMP2 or BARF1, comprising the steps of:
  cloning the genetic information for the antibody reagent according to claim 1 into the viral genome
  expressing the said antibody on the viral coat of the said viral particles.

Antibody reagents are used to genetically influence or alter the receptor binding characteristics of viruses currently used for gene therapy approaches, which provides such viruses with improved specificity for binding to cq. penetration of defined target cells, thus improving their therapeutic specificity and effectiveness (see, e.g.: Dimitriev et al, J. Virol. (2000) 74: 6875).

In the above-mentioned viral system according to the invention, the viral particles will be able to bind EBV infected cells expressing LMP1, LMP2 or BARF1 on their cell surface. Such a viral particle may be genetically engineered such, that it comprises genetic information for a toxin or any alternative bioactive molecule that is expressed upon binding and penetration of the viral particle into the EBV infected cell, resulting in specific infection of the LMP1, LMP2 or BARF1 expressing cells.

As the antibody reagent specifically binds to EBV+ tumour cells, such a reagent is particularly useful as diagnostic or therapeutic agent in patients carrying EBV positive tumours. Antibody reagents may be linked to a radiolabel ($I^{131/125}$, Technetium, ea.), toxin (Ricin A, Diphteria Toxin, ea.), prodrugs or in fact any biological response modifier (IL-12, IP9, ea.), thereby mediating improved delivery of the label to the target cell. This may result in specifically enhanced diagnostic visibility of small nests of tumour cells (e.g. when using radiolabel) or eliminating of the targeted cells (e.g. either when using radiolabel or toxin) or attracting and activating immune or bystander cells near the target cell (e.g. when using lymphokine). (Examples: M. J. Glennie and P. W. M. Johnson, Immunol. Today (2000) 21: 403, Van Spriel et al, Immunol. Today (2000) 21: 391; P. J. Hudson, Curr. Opinion Immunol. (1999) 11: 548); Helfrich et al., J. Immunol. Meth. (2000) 237: 131).

The peptides, polynucleotides and antibody reagent according to the invention can advantageously be used in a medicament in particular for treatment of EBV infection. The peptides according to the invention can be used as immunogen in a medicament, such as a vaccin, i.e. as active ingredient for treatment of EBV-infection.

Upon administration of such a medicament to a subject, the immune system of the said subject will generate antibodies against the peptides, which antibodies will also be reactive against EBV+-cells, expressing proteins comprising the said peptide sequence on their cell surface. Accordingly, polynucleotides according to the invention can be used in a medicament, in particular for treatment of EBV-infection. Upon administration into a subject, the polynucleotides can be transcribed and/or translated into the peptides according to the invention, therewith providing the immunogen as discussed above. Also, the antibody reagents according to the invention can be used in a medicament, in particular for treatment of EBV-infection. In that case, the antibody reagent is preferably coupled to a toxin or other biological modifier. The said toxin or modifier can, upon administration of the antibody reagent to a EBV-infected patient, be coupled in a specific manner to EBV+ cells (i.e. EBV+ tumour cells) of the individual, leading to a specific elimination of substantially only EBV+ cells.

The peptides, nucleic acid sequences and antibody reagents of the invention may preferably be combined with various components to produce pharmaceutical or diagnostic compositions or medicaments of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular or transdermal administration. Typically, each antibody reagent may be administered at a dose of from 0.01 to 30 mg/kg body weight, preferably from 0.1 to 10 mg/kg, more preferably from 0.1 to 1 mg/kg body weight. For example, in the art, anti-CD20 rituximab is used at 375 mg/m² body surface, which equals about 10 mg/kg body weight (Yang et al, Blood 96 (2000), 4055-4063) and anti-CD25 Daclizumab is used at 1 mg/kg (Vicenti et al, New Engl. J. Med. 338 (1998), 161-165).

Polynucleotides/vectors encoding a peptide according to the invention may be administered directly as a naked nucleic acid construct, preferably further comprising flanking sequences homologous to the host cell genome. When the polynucleotides/vectors are administered as a naked nucleic acid, the amount of nucleic acid administered may typically be in the range of from 1 μg to 10 mg, preferably from 100 μg to 1 mg.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration. It is also possible to incorporate a transfection agent, such as the above-discussed cationic agents in the composition or medicament.

The routes of administration and dosages described are intended only as a guide since a skilled practitioner will be able to determine readily the optimum route of administration and dosage for any particular patient and condition.

In particular, the invention relates to a method for diagnosing EBV infected cells, especially EBV+ malignant cells and EBV mediated diseases, comprising the steps of:
  taking a sample of cells of an individual, suspected of carrying said infected cells of disease;
  contacting the antibody reagent with the said cells;
  reacting the antibody reagent with the said cells, forming a complex of antibody reagent, bound to an EBV infected cell;
  assaying for the presence of the said complex.

Samples comprise body fluids, such as blood and isolated blood leukocyte preparations, peritoneal, cerebrospinal or pleural fluid aspirates that may contain potential EBV-carrying tumour cells or tissue biopsy specimens or cells obtained thereof. It is advantageous to remove non-bound antibodies before the assaying step, e.g. by one or more washing steps. Assaying for the presence of the complex can be done according to techniques known in the art, by e.g. using known immunofluorescence or immuno-enzyme staining techniques by e.g. spinning stained cells onto glass slides and analysing them by fluorescence microscopy, or by analysis of stained cells in suspension using FACS-techniques or by using in situ immunohistochemical staining techniques.

For example EBV+-tumour cells or circulating EBV-infected cells in blood may be visualised in situ by means of indirect anti-LMP1 antibody staining in fixed and permeabilized tumour tissue sections of patients with various EBV-associated cancers and/or acute primary EBV-infection. Alternatively, antibody reagents may be used to directly visualise viable cells using FACS-analysis (see e.g. Jiwa et al, J. Clin. Pathol. (1995) 48: 438; Wagner et al, Clin. Diagn. Lab. Immunol. (1995) 2: 696; Herzenberg et al, Immunol. Today (2000) 21; 386).

In another embodiment, the invention relates to a method for specifically eliminating cells expressing LMP1, LMP2 or BARF1 or parts thereof on their cell surface ex vivo, comprising the steps of:
  isolating a number of cells from an individual
  contacting the isolated cells with an antibody reagent according to the invention
  negatively selecting the cells expressing LMP1, LMP2, of BARF1 on their cell surface, wherein cells, not expressing LMP1, LMP2 or BARF1 on their cell surface survive. In this way, the isolated cells, not expressing the EBV specific cell surface proteins survive and are 'cleaned' from any present EBV-positive (tumour) cells. The method is particularly important when the surviving cells are to be reimplanted into the individual.

Methods for negatively selecting cells are known in the art; the antibody reagent may e.g. be coupled to e.g. magnetic beads, a lysing function, a function mediating complement deposition on the surface of cells binding the antibody reagent of directing killer cells to the surface of these cells. The skilled person will be aware of numerous other methods for negative selection in vitro incubation with target cells according to the invention may also be contemplated as a combination of the contacting and selecting step. Lysing the cells is a preferred way of negative selection.

The above-mentioned method can be used for tumour cell purging and is especially useful when bone marrow cells are isolated from the individual, that are to be reimplanted into the said individual after the individual has been subjected to radiation or chemotherapy. According to the invention, bone marrow specimens may be cleaned from tumour cells prior to reinfusion into the patient by incubation with purified antibody reagent and subsequent contact with complement or killer cells, leading to the specific elimination of those cells that have bound the antibody reagent to their surface (see e.g. Berkahn, J. Hematother, Stem Cell Res. (2000) 9: 147; Schroder et al, Clin. Cancer Res. (2000) δ: 2521).

EXAMPLES

General Methodology Reference

Although in general the techniques mentioned herein are well known in the art, reference may be made in particular to Sambrook et al., Molecular Cloning, A Laboratory Manual (1989) and Ausubel et al., Current Protocols in Molecular Biology (1995), John Wiley & Sons, Inc.

Example 1

Design of LMP1, LMP2 and BARF1 Derived Peptides with a Putative Extracellular Localisation The amino acid sequences of LMP1, LMP2 and BARF1 were retrieved from the Swiss-Prot or Genbank database.

The aim was to define and demonstrate the existence of extracellular domains on these proteins as expressed in naturally infected and transformed. (tumour) cells.

Thereto, as a first step the amino acid sequences derived from DNA encoding the LMP1, LMP2 and BARF1 proteins were used and the putative transmembrane domains were localised by hydrophobicity analysis using the GCG protein analysis program, supra.

This analysis revealed LMP1 to contain a hydrophilic N-terminus of about 20 amino acids followed by 6 subsequent hydrophobic domains, forming 6 repeated putative intra membrane helices connected by three short intracellular charged sequences and three putative extracellular domains, which are referred to as LMP1 loop -1, -2 and -3 (FIG. 1), then followed by a hydrophilic C-terminus covering amino acids 186-386.

Figure 2:
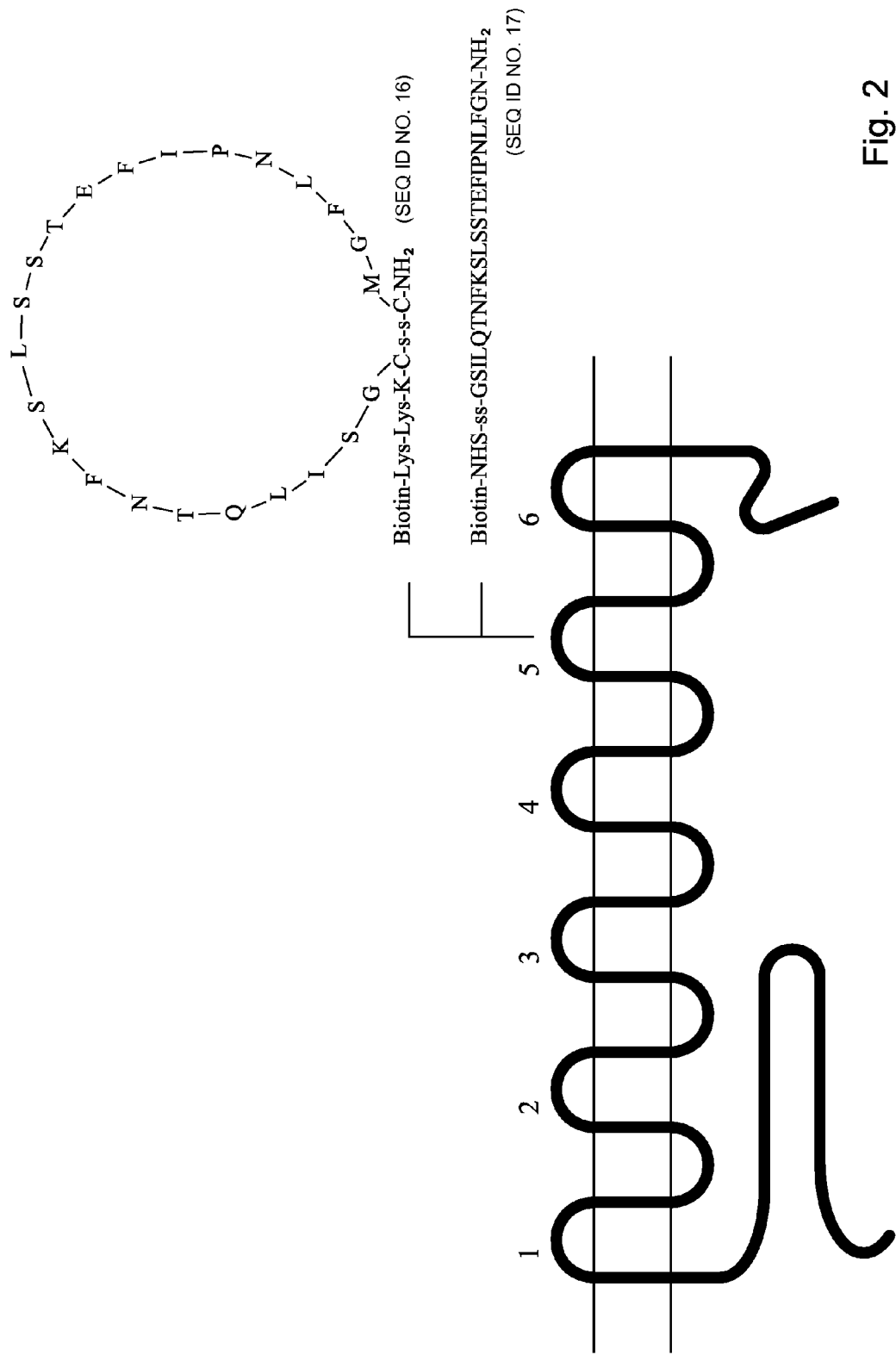
FIG. 2 is a schematic diagram of the putative structure of LMP2.

LMP2 contained hydrophilic N- and C-terminal sequences separated by 12 putative transmembrane domains membrane suggestive of 6 membrane crossings and with 6 extracellular domains referred to as LMP2 loop1-6 (FIG. 2).

Analysis of the BARF1 gene revealed a short N-terminal domain with a potential signal sequence, followed by a single short hydrophobic domain and a large C-terminal domain characteristic of "classic" type-I transmembrane proteins with a large and possibly glycosylated extracellular domain.

For the selection and synthesis of peptides potentially mimicking the extracellular LMP1 and LMP2 loops, two strategies were followed:
1. Linear peptides were made according to Seq.ID1-3 for LMP1 and Seq.ID 4-9 for LMP2, which include all of the putative extracellular amino acids corresponding to the individual loops, flanked on each side by two hydrophobic amino acids putatively forming the start of the membrane anchoring α-helix.
2. Structurally constraint circular peptides were made using the sequence of the linear peptides defined above, but flanked on each side by an additional cystein residue, which were oxidised after synthesis to form a covalent S—S bond, thereby forcing a circular structure upon the peptide.

Each peptide was further synthesised with and without an additional stretch of 1-3 Lysine residues at the N-terminus to facilitate covalent coupling to a carrier protein using glutaraldehyde or alternatively to facilitate covalent coupling of a biotin residue with or without a cleavable linker to facilitate the coupling of peptides to immobilised streptavidin.

Figure 1:
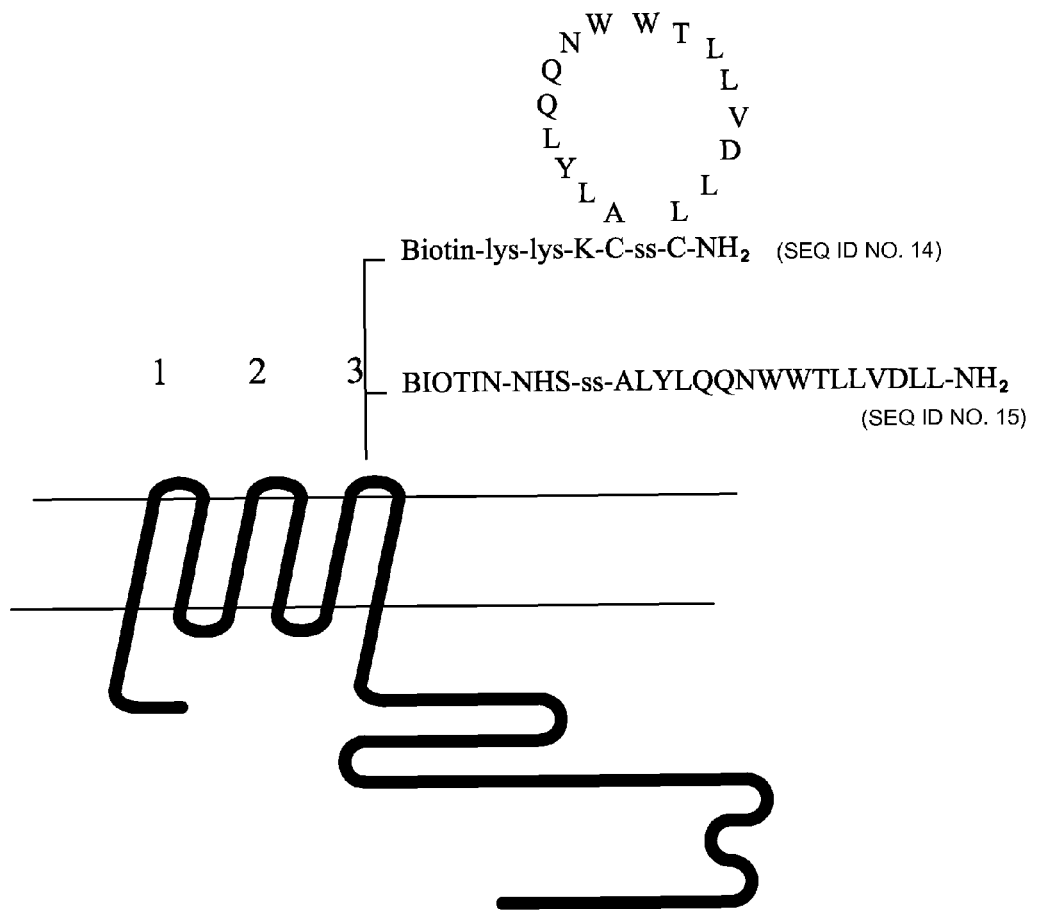
FIG. 1 is a schematic diagram of the putative structure of LMP1.

Examples of the synthesis strategy for loop-3 of LMP1 and loop 5 of LMP2 are indicated schematically in FIGS. 1 and 2 respectively.

For BARF1 specific peptide synthesis, sequences were selected from Seq.ID10, 12 and 13 incorporating several charged amino acids plus at least one proline residue, the combination of which enhances the surface probability of the selected sequences.

Example 2

Generation of Antibody Reagents Reactive with Putative Extracellular Domains of LMP1, LMP2 and BARF1 Proteins by Immunisation with Designated Putative Extracellular Domain-Specific Peptides and Demonstration of the Existence of these Extracellular Domains in EBV-Transformed Cell Lines There is no direct proof for the existence and accessibility of LMP1, LMP2 and BARF1 domains on the outer surface of naturally EBV-infected transformed (tumour) cells.

Therefore, the first aim was to create specific reagents that would define such domains and would allow the demonstration of the functional accessibility of these domains.

Methods:

Peptides were made using fMoc chemistry using a solid phase peptide synthesizer (Applied Biosystems, USA). Following acid cleavage from the resin, peptides were washed repeatedly with diethylether and purified by RP-HPLC (Beckman System Gold). When relevant, peptides were circularised by oxidising the sulphydroxy-groups. Finally peptides were freeze-dried and stored at 4° C. in 1-10 mg aliquots.

Purified peptides were dissolved by slow heating to 50° C. in dimethylsulfoxide (DMSO) to a concentration of 10 mg/ml and diluted 1:10 in saline prior to use for immunisation of rabbits or guinea pigs. For each immunisation 200 ug peptide was incubated with 15 µl of 2.5% glutaraldehyde and 1.2 mg purified keyhole limpet hemocyanine (KLH) or 0.5 mg tetanus toxoid (TTd) in the dark at room temperature (RT) for at least 1 hour (h). The coupling was stopped with 60 µl stabilising buffer (1 M Glycine, pH 8.0) in the dark for 1 h at RT.

PBS was added to a final volume of 1 ml and mixed with an equal volume of Freunds adjuvant.

This preparation was used for immunisation of animals by subcutaneous injection (Table 1).

TABLE 1

Summary of the animal sera used in the examples.

| Animal | Antigen | Sequence used | Adjuvans |
|---|---|---|---|
| K97-31 | TTd-LMP1-loop1 | Seq. ID. 1 | FCA/FIA |
| K97-54 | KLH-LMP1-loop1 | Seq. ID. 1 | FCA/FIA |
| K97-55 | TTd-LMP1-loop3 | Seq. ID. 3 | FCA/FIA |
| K97-56 | KLH-LMP1-loop3 | Seq. ID. 3 | FCA/FIA |
| K121 | LMP1(181-386)-βGal | Intracellular domains of LMP1 linked to βGalactosidase | FCA/FIA |
| K97-47 | KLH-LMP2-loop2 | Seq. ID. 5 | FCA/FIA |
| K97-43 | KLH-LMP2-loop5 | Seq. ID. 8 | FCA/FIA |
| Gp-N | KLH-BARF1-AA40-79 | Seq. ID. 10 | FCA/FIA |
| Gp-M | KLH-BARF1-AA155-188 | Seq. ID. 12 | FCA/FIA |
| Gp-C | KLH-BARF1-AA180-221 | Seq. ID. 13 | FCA/FIA |

K = rabbit,
Gp = guinea pig,
N = N-terminal,
M = Middle,
C = C-terminal
TTd = tetanus toxoid,
KLH = Keyhole Limpet Hemocyanine
FC(I)A = Freunds (In)Complete Adjuvant Results:

1. Polyclonal Antibody Reagents Directed Against Putative Extracellular Domains of LMP1, LMP2 and BARF1 in Sera from Peptide Immunised Animals:

Pre-serum and serum was obtained from rabbits after the third immunisation with the respective peptides (Table 1). Sera and protein A purified antibody reagents (Ab's) from these sera were tested for LMP1-protein and LMP1 loop-peptide specific reactivity using ELISA assays with purified LMP1 protein or LMP1 loop peptides coated to the solid phase (FIG. 3A-D) and by immunoblot using extracts from EBV+ RAJI cells and EBV− RAMOS cells (FIG. 4A). These methods are similar as described in Meij et al. J. Infect. Dis. (1999) 179 :1108-1115.

Using the peptide-ELISA's a clear and specific antibody response was seen after the third immunisation and no cross-reactivity between the different loops was seen with the individual hyperimmune sera (FIG. 3A-D).

Figures 3E, 3F:
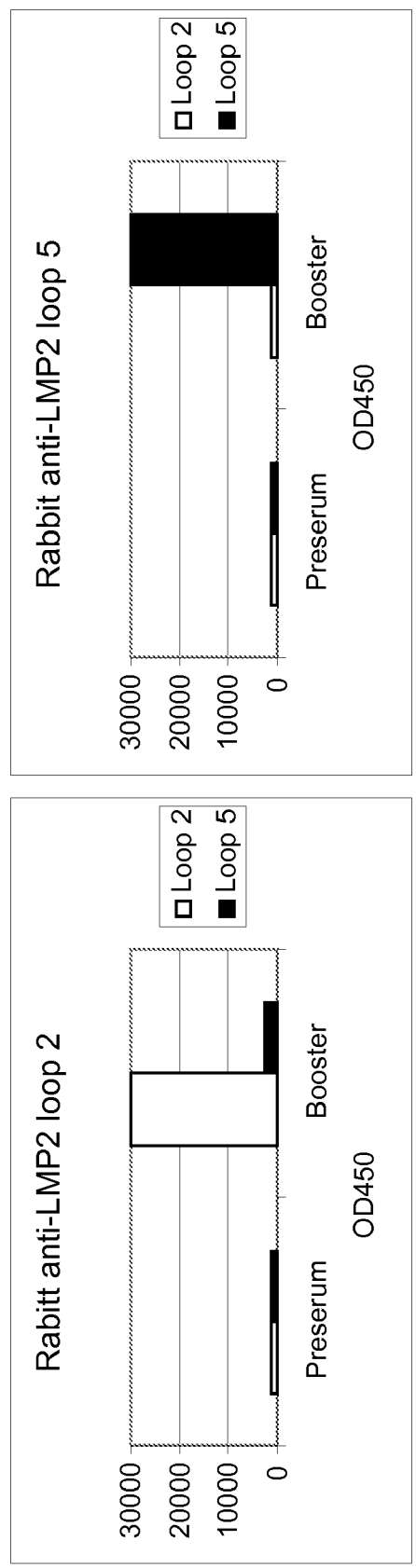
FIGS. 3 A-D show antibody reactivity measured in LMP1 peptide- or purified LMP1 protein-coated ELISA of rabbit anti-LMP1 loop sera (1:100) before and after immunisation (Booster) (A,B) and of rabbit serum-derived purified Ab's (C, D)
Figure 3H:
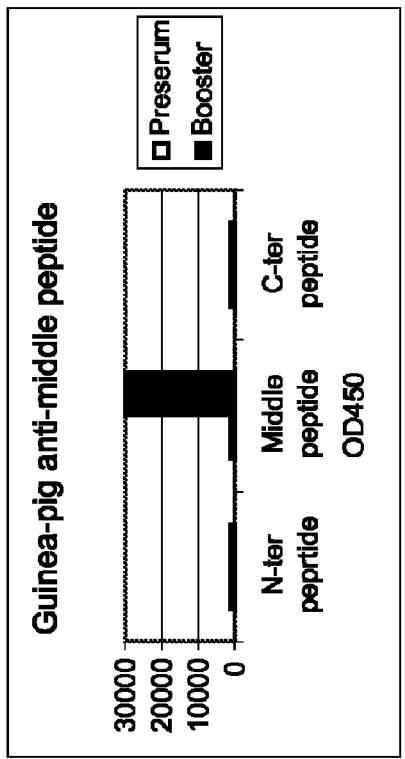
Figure 3G:
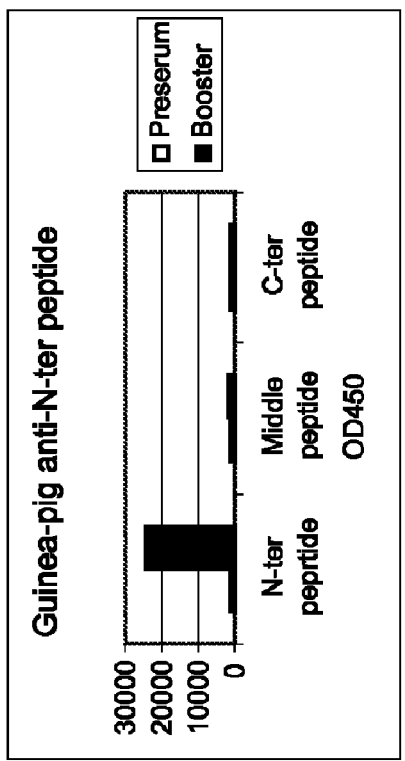
Figure 3I:
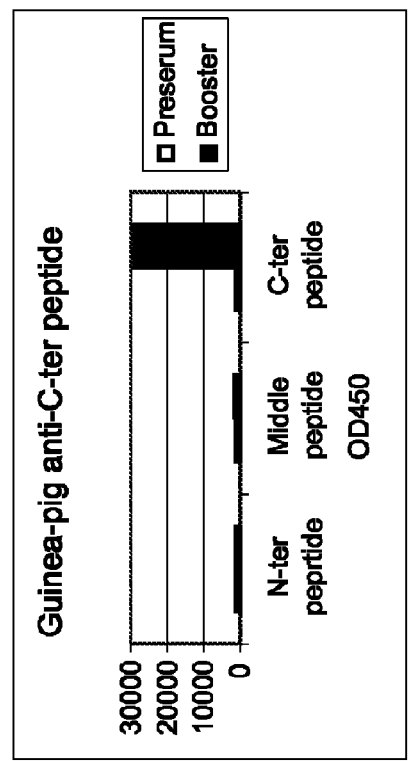

Reaction against LMP1 loop 1 was weaker than for LMP1 loop 3, which may be explained by the fact that the peptide representing loop1 is smaller than the peptide representing loop 3. After purification of the Ab's on Protein-A Sepharose (Pharmacia, Uppsala, Sweden) an even higher reactivity is seen against the peptides (FIG. 3C-D).

Ab's from the immunised rabbits also recognised purified recombinant LMP1 derived from the Baculovirus expression system (Meij et al. J. Virol. Meth. (2000) 90:193-204). With purified Ab's the reaction against LMP1 loop 1 is also lower than against loop 3, similar as found with the peptide-ELISA.

Figure 4:
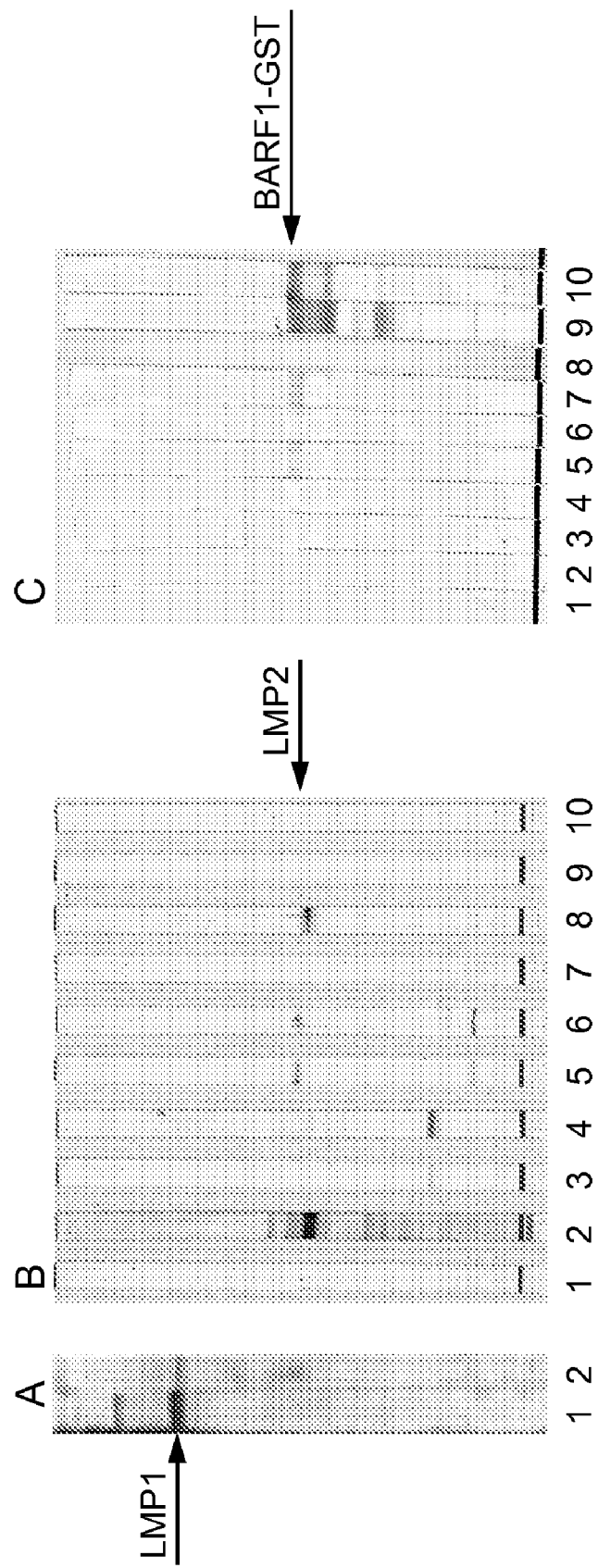
FIG. 4 shows an immunoblot of full length LMP1 (A), LMP2 (B) and BARF1-GST protein (C), probed with different sera from animals immunised with the relevant peptides as described in FIG. 3.

Reactivity of Ab's in sera from peptide-immunised animals with intact full length LMP1, LMP2 and BARF1 proteins was analysed by immunostaining of western blots as shown in FIG. 4. Antigens applied to the blot consisted of partially purified extracts of LMP1, LMP2 proteins expressed in the Baculovirus-SF9 insect cell system (Meij et al., 1999) and GST-BARF1 fusion protein expressed in E. coli (unpublished data).

Immunoblot analysis, using purified Ab's reactive with LMP1 loop 1 and 3, shows a clear band at the appropriate position of 62 kD (FIG. 4A) and thereby confirming their binding to the full length protein.

Similarly, LMP2 loop-specific antibody reagents were developed by immunisation of rabbits with LMP2 derived loop 2 and loop 5 peptides. The resulting sera and Ab's contained therein showed LMP2 and LMP2 loop-specific reactivities in ELISA and immunoblot (FIGS. 3 E-F and 4B).

Similarly, BARF1-specific Ab's were made by immunisation of guinea pigs with BARF1-derived peptides representing putative extra-cellular domains (FIGS. 3 G, H, I and 4C).

The results of these studies indicate that immunisation with LMP1 loop-1,-2,-3, LMP2 loop-2,-5 and various BARF1 derived peptides yield antibody reagents specifically reactive with the respective loop-peptides as well as the full length LMP1, LMP2 and BARF1 protein.

2. Staining of LMP1 and LMP2 in Fixed JY Cells or Unfixed Viable JY Cells.

JY cells, a human B-cell line created by EBV B95-8 infection and transformation of human primary peripheral blood B-cells were grown to the log-phase, washed with PBS and spun onto glass slides and subsequently fixed with cold acetone.

To reveal the presence of LMP1 and LMP2 in these cells and to demonstrate the binding of anti-LMP1 and anti-LMP2 loop Ab's with the natural proteins in EBV+ cells, fixed cells were incubated with appropriate dilutions of anti-loop Ab's or control Ab's reactive with intracellular domains of LMP1 and LMP2, washed and bound antibodies were visualised by second antibodies conjugated to HRP and DAB staining.

An example of LMP1 staining is shown in FIG. 5A, which reveals a rather heterogeneous staining characteristic for LMP1, which is known to aggregate in intracellular and plasma membranes. Also the variable staining of individual cells is characteristic but yet unexplained.

To verify whether Ab reagents created by animal immunisation with putative extracellular domains of LMP1, LMP2 or BARF1 indeed would react with the outer surface of viable EBV-transformed tumour cells, and thus confirming the existence and accessibility of these putative extracellular domains, indirect immunofluorescence staining of viable EBV+ JY and EBV− RAMOS cells was done. The procedure was similar as described by Middeldorp et al. J. Virology (1985) 54:240-244. JY and Ramos cells were grown to the log-phase and washed in Hank's buffer at +4° C. and incubated with antisera or purified Ab's at appropriate dilutions in ice-cold Hank's solution for 1 hour on melting ice, washed with icecold saline and incubated with swine-anti-rabbit-FITC diluted in Hank's solution and washed again. Stained cells were spun onto glass slides using a cytocentrifuge, fixed with a 1:1 mixture of icecold water free acetone/methanol and analysed by fluorescence microscopy.

It was found that antibodies directed against LMP1 loop3 show a clear brilliant and patchy rim around the plasma membrane of the JY cells and no reaction around the RAMOS cells. Staining for LMP1 loop1 was relatively weak on JY-cells (data not shown). It is possible that the lower intensity of the staining for loop 1 was due to the lower immune response or reduced affinity of Ab's against loop 1.

Similar results were obtained for anti-LMP2 loop2 and anti-LMP2 loop5 antisera.

These results demonstrate for the first time the presence and accessibility of LMP1 and LMP2 derived loop sequences on the surface of EBV transformed cells, such as JY.

3. Induction of Target Cell Lysis by Anti-Loop Ab's Using Complement Lysis:

Purified Ab's against LMP1 loop1 and 3 were used in a standard complement dependent $^{51}$Cr release test as described by Middeldorp et al. J. Infectious Diseases (1986) 153:48-55.

JY and Ramos cells were grown to the log-phase and washed in fresh culture medium without serum. Aliquots of rabbit antisera or purified Ab's were added at appropriate dilutions in medium, Immediately followed by freshly obtained serum from non-immunized SPF-rabbits to provide a source of complement. The maximal lysis was determined by adding 1% Triton X-100 instead of rabbit complement, positive controls consisted of rabbit anti-52 Microglobulin antibodies (DAKO, Denmark) and negative controls consisted of pre-immune sera from all rabbits analysed.

The results from these experiments show that Ab's in sera from animals immunised against LMP1 loop 3 were clearly capable of mediating specific lysis of LMP1 expressing JY cells. RAMOS-cells were not susceptible to lysis using Ab's against loop3 and complement.

For Ab's against loop 1 the results were only borderline positive, possibly related to the low Ab-titer obtained.

These results demonstrate that anti-LMP1, LMP2 and BARF1 loop-peptide specific antibody reagents define and recognise cell surface exposed domains derived from the native protein and are capable of mediating the lysis of cells expressing these domains.

Overall, these results also demonstrate that specific immunisation with synthetic peptides of putative extracellular domains of LMP1, LMP2 (and BARF1) is capable of inducing immune responses directed against cell surface exposed regions of these proteins and that such responses can mediate the lysis of cells exposing these domains.

Example 3

Generation of Human Antibody Reagents Reactive with the Putative Extracellular Domains of LMP1, LMP2 or BARF1 from a Human Phage-Antibody Library by Phage Display Selection with Synthetic Loop-Domain Specific Peptides The generation of mouse and/or rat monoclonal antibodies by animal immunisation and the hybridoma cell-fusion technique of Kohler and Milstein is well known. However, this methodology does not readily allow generation of human monoclonal antibodies, which are the preferred antibody reagents for in vivo (ex vivo) therapeutic applications. Since The LMP1, LMP2 and BARF1 proteins are hardly immunogenic in man (Meij et al. 1999), the production of human antibodies with specificity for the extracellular domains of LMP1, LMP2 and BARF1 is not straight forward.

Therefore, an alternative approach was tried by using the novel and specifically constructed (now defined) extracellular domain peptides, described in example 1 and 2, to select for specific human antibody reactivity in phage antibody libraries expressing the human antibody repertoire as single chain antibodies or as Fab fragments displayed on the phage surface.

Only selections with LMP1-derived reagents will be demonstrated.

Methods:

a. Library Construction:

For this study, either a single chain antibody phage library as described by Vaughan et al., supra, or a human Fab fragment library as described by de Heard et al., supra, was used.

Said libraries are so-called expression libraries, e.g. containing up to $10^{15}$ different phages (clones), each containing a different fragment of the human genome.

For selection of LMP1-, LMP2- and BARF1-reactive phages a similar peptide synthesis strategy was used as described in example 1-2 and shown in FIGS. 1 and 2.

Either linear or circularised constraint peptides were used. All peptides contained a biotin moiety which was linked to the N-terminus of the peptide by means of a cleavable linker, allowing epitope-selected peptide-binding phages to be released after sequestration on Streptavidine-coated magnetic beads.

Peptides relevant for this example are shown in table 2.

TABLE 2

LMP1 derived peptides used in this study for phage selection purposes (AA sequences derived from the B95-8 prototype LMP1)

| Peptide (AA position) | Sequence |
|---|---|
| LMP1-Loop1-Lin (41-56) | H2N-*KKKC*-YIVMSDWTGGALLVLY-*C*-COOH |
| LMP1-Loop2-Lin (94-108) | H2N-*KKKC*-LIALWNLHGQALFLG-*C*-COOH |
| LMP1-Loop3-Lin (157-172) | H2N-*KKKC*-ALYLQQNWWTLLVDLL-*C*-COOH |
| LMP1-Loop1-Bio-SS-NHS | Bio-SS-NNS-*KKKC*-YIVMSDWTGGALLVLY-*C*-COOH(*) |
| LMP1-Loop2-Bio-SS-NHS | Bio-SS-NHS-*KKKC*-LIALWNLHGQALFLG-*C*-COOH(*) |
| LMP1-Loop3-Bio-SS-NHS | Bio-SS-NHS-*KKKC*-ALYLQQNWWTLLVDLL-*C*-COOH(*) |
| LMP1-Bio-Loop1-CIR | Bio-*KKC*-YIVMSDWTGGALLVLY-*C*-COOH* |
| LMP1-Bio-Loop2-CIR | Bio-*KKC*-LIALWNLGQALFLG-*C*-COOH* |
| LMP1-Bio-Loop3-CIR | Bio-*KKC*-ALYLQQNWWTLLVDLL-*C*-COOH* |

Bold-italic = AA's added for technical reasons, not included in the natural sequence.
*these peptides are circularized by covalent crosslinking of the *C-C* group b. Screening, Selection and Characterisation of the LMP1 Loop1-3 Reactive Phages Using Synthetic Peptides:

For the selective panning of LMP1-loop peptide binding phages from random phage repertoires, biotinylated peptides of LMP1 loop1, 2 and 3 were immobilised to streptavidin-magnetic beads (Dynall, Norway) for 30 min. at RT. Non-Specific binding places were blocked by using 3% dry milk powder (Marvel) and 10% DMSO in PBS for 1 hr. During this time phages were also incubated with 3% Marvel and 10% DMSO in PBS for 1 hr at RT. After 1 hr phages and streptavidin-magnetic beads (with or without immobilised peptides) were added together and incubated for 1 hr at RT. The magnetic beads were subsequently washed 10 times with PBS and specific bound phages were eluted by adding 50 mM DTT in H2O for 10 minutes to reduce the cleavable S—S linker.

After the third and fourth round of selection 46 single phage clones or colonies were isolated from the selected phage populations and these were screened for production of phage-bound or soluble Fab's reactive with the corresponding peptides or full length LMP1 protein (see methods for ELISA's and immunoblot analysis in example 2).

Fingerprint analysis, production of phages and production of soluble Fab's were performed as described by McCafferty et al (Nature (1990), 348: 552), Griffiths et al (EMBO J. 1994 13:3245), Marks et al (J. Mol. Biol. (1991) 222: 581); Vaughan et al., Nature Biotech. (1996) 14:309-314 and de Heard et al J. Biol. Chem. 274 (1999); 18218-18230.

Results:

1. Selection Ab-Reactivity Against the Extracellular Parts (Loop 1, 2 and 3) of LMP1 in Human Fab Phage-Libraries Using Synthetic Peptides as Antigen:

In a first series of experiments a single chain antibody library as described by Vaughan was used to select phages with LMP1-loop peptide-binding activity.

Although specific loop-peptide binding phages were found that did not showed any binding to the streptavidine control plates, detailed analysis revealed that all peptide binding phages showed similar reactivity to different individual circularised constraint peptides used in the selection procedure. No reaction was seen with the linearized form of these peptides. Therefore it was concluded that the common structure in these peptides, being the S—S bond and adjacent lysine groups (see table 2) was responsible for generic binding to the individual phages. Indeed a non-related peptide with a similar 3-Lysine S—S constraint linker confirmed the generic character of the selected phages. Additional selections did not reveal any peptide-specific binding.

From these experiments it was concluded that the Vaughan type library either produced ScAb's with insufficient binding characteristics or contained too little Ab-diversity to rapidly provide a source of LMP1 loop-peptide specific binders and subsequently a switch was made to use a human Fab phage library with extended diversity as described by de Haard et al. (1999).

The new selections using a human Fab library are described in detail below.

Binding of the phages to the peptides was done in 10% DMSO, 3% Marvel in PBS due to the low solubility of the hydrophobic peptides.

From previous experiments is became clear that viability of phages was not influenced by the presence of 10% DMSO (data not shown).

For LMP1-Loop-1 three rounds of selection were done and for Loop-2 and -3 four rounds of selection were done.

Table 3 summarizes the results of the different rounds of selection.

TABLE 3

Results of the different rounds of phage selection using LMP1-derived loop-specific synthetic peptides.

| Round | Input | Output | o/i ratio | Enrichment |
|---|---|---|---|---|
| Loop 1 peptide | | | | |
| 1 | $8.8 * 10^{12}$ | $6.4 * 10^5$ | $7.3 * 10^{-8}$ | |
| 2 | $1.0 * 10^{13}$ | $7.4 * 10^5$ | $7.4 * 10^{-8}$ | 1 |
| 3 | $1.9 * 10^{13}$ | $1.3 * 10^9$ | $6.8 * 10^{-5}$ | 919 |
| Loop 2 peptide | | | | |
| 1 | $8.8 * 10^{12}$ | $1.0 * 10^4$ | $1.1 * 10^{-9}$ | 1 |
| 2 | $1.6 * 10^{13}$ | $2.0 * 10^4$ | $1.3 * 10^{-9}$ | 2 |
| 3 | $1.4 * 10^{13}$ | $1.8 * 10^6$ | $1.3 * 10^{-7}$ | 100 |
| 4 | $1.5 * 10^{13}$ | $4.8 * 10^6$ | $3.2 * 10^{-7}$ | 3 |

TABLE 3-continued

Results of the different rounds of phage selection using LMP1-derived loop-specific synthetic peptides.

| Round | Input | Output | o/i ratio | Enrichment |
|---|---|---|---|---|
| Loop 3 peptide | | | | |
| 1 | $8.8 * 10^{12}$ | $1.4 * 10^6$ | $1.6 * 10^{-7}$ | |
| 2 | $1.5 * 10^{13}$ | $1.5 * 10^6$ | $1.0 * 10^{-7}$ | 1 |
| 3 | $2.3 * 10^{13}$ | $8.6 * 10^8$ | $3.7 * 10^{-5}$ | 370 |
| 4 | $2.0 * 10^{13}$ | $8.8 * 10^8$ | $4.4 * 10^{-5}$ | 1 |

From Table 3 it is clear that significant enrichment took place in round three of the selection and additional selection rounds did not result in higher enrichment.

From round 3 and 4, 46 colonies were picked and induced for phage-production. Subsequently, the phage containing culture medium was tested in peptide-coated ELISA to check for specificity with the individual peptides or streptavidine as a control.

Phage populations from different selections were tested for cross-reactivity by analysing their binding to alternative peptides for which they were not selected.

The overall ELISA results are shown in FIG. 6. Therefrom, it is clear that the selected phages display a high specificity for the selection peptides and do not cross-bind to alternative peptides nor to streptavidine. It can be seen from the examples for loop-2 and loop-3 that some phage clones reactive with linear loop peptides may also display reactivity with S—S circular constraint peptides, which are considered to mimic the natural loop structure in LMP1 more closely.

Therefore, these experiments demonstrate that human antibody reagents can be specifically selected from large enough random antibody phage libraries using the specifically designed loop peptides representing extracellular domains of LMP1, LMP2 and BARF1.

2. Characterization of Human Antibody Reagents Expressed by Selected Phages.

FIG. 7 shows a representative DNA-restriction analysis for a selected number of individually picked clones I order to define the clonotypic variation between phage clones selected with the different peptides.

The results reveal that different fingerprints (clonotypes) can be observed within and between differently selected phage populations, but that within a population of phages reactive with the same loop peptide similar if not identical clonotypes are encountered. This most likely reflects the independent isolation of phages with a similar if not identical antibody idiotype structure for binding to the peptide antigen.

For example within phages reactive with LMP1 loop1, the individually isolated clones 1, 2 and 4 show a very similar fingerprint pattern, whereas clones 6 and 9 and clones 5 and 10 have a similar clonotype among themselves but which is clearly different from each other and from clones 1, 2 and 4. Clones 3 and 7 and 11 appear to be distinct from the ones named before, yet all clones react similarly with LMP1 loop 1 peptide.

Analogous, from selections with LMP1 loop3 peptide, clones 3,6,7,8,9 and 13 appear to be rather similar but of different fingerprint signature compared to clones 1,4,5,10 (etc.).

Table 4 summarizes the overall recovery of LMP1 loop 1-3 specific clones from selections after round 3.

TABLE 4

Overall characterisation results for different LMP1-specific phage selections of round 3.

| LMP1 Loop peptide | Clones obtained | Different fingerprints | Soluble Fab expression |
|---|---|---|---|
| 1 | 14 | 8 | 5 |
| 2 | 41 | 2 | 2 |
| 3 | 29 | 14 | 10 |

Overall, selection with LMP1 loop-1 peptides yielded 14 clones with 8 different clonotypes, as reveiled by DNA fingerprint analysis. Selection for LMP1 loop-2 yielded 41 clones with only 2 clonotypes and selection for LMP1 loop-3 yielded 29 clones with 14 different clonotypes.

From Table 4 it is clear that the diversity of phages reactive against loop 2 is low. Only 2 different fingerprints are detected. Taken in account that loop 2 is the shortest peptide of all, this may explain the low diversity. This is further supported by the finding that among the reactive phage clones of loop 2 6/6 (100%) tested were also reactive with the circularised loop 2.

The diversity of phages reactive with LMP1 loop 3 was the highest, which correlates well with the larger size of this loop and the presence of two bulky tryotophane residues in the middle of the loop. In a limited evaluation of different clones, 3/6 (50%) loop3 selected phage clones also displayed reactivity with the circular constraint peptide of loop 3.

The results show that different clonotypes may be selected from random antibody libraries, which individually show defined reactivity with the specific extracellular domains of LMP1, LMP2 or BARF1.

3. Expression of Phage-Antibody Reagents as Soluble Fab Antibody Reagents.

Since phage-bound antibody reagents are not compatible with future therapeutic application, it is necessary to obtain purified antibody reagents which retain the original antigen-binding specificity.

Therefore, to analyse the possible production of soluble Fab-reagents (Fab's) from the selected phage clones, Fab protein production was analysed for different clones by IPTG mediated induction of phage protein expression in *E. coli*.

The Fab's produced in this way from different loop-peptide selected phages (as indicated in Table 4) were analysed for reactivity with the intact LMP1 protein as shown in FIG. 8 and by peptide ELISA (data not shown).

FIG. 8 shows an immunoblot analysis which reveals the (weak) reactivity of soluble Fab's to purified full length LMP1.

Several soluble Fab's from different phage clones were reactive against the full length LMP1 protein.

For loop 3 reactive phages, 10/14 (71%) genetically different clones were shown to produce soluble Fab's that were reactive against the circular loop 3 peptide by ELISA and showed a detectable reaction with the LMP1 protein.

It has to be taken in account that no effort was made in optimising refolding of the expressed Fab's or optimising expression in the clones that did not produce soluble Fab's.

Also phage producing colonies from round 4 of the selections using loop 2 and 3 were picked and analysed. There were no major ELISA-reactivity or genetic differences in the phages that produced specific Fab's and were picked in round 4 as compared to round 3.

These results demonstrate that soluble human antibody reagents having a defined and distinctive reactivity towards the natural full length proteins LMP1, LMP2 and BARF1 can be produced from phage antibody populations, which are selected with designer peptides.

Overall the results from example 3 show that distinct human antibody reagents can be selected from random antibody libraries, created by genetic cloning of antibody repertoires, using specifically designed loop-domain peptides derived from putative extracellular domains of LMP1, LMP2 and BARF1. Results also show that such antibody reagents can be expressed and produced in soluble form, detached from generic library components, and that such antibody reagents are capable of specific binding to the intact full length protein.

Example 4

Selection of Human Fab Antibody Reagents Reactive with Extracellular Domains of LMP1 from a Human Antibody Phage Library Using Intact and Viable EBV-Transformed Lymphoblastoid JY Cells Expressing the Natural Form of LMP1

As an alternative or additional selection step in the design of human antibody reagents reactive with native extracellular domains of LMP1, LMP2 and BARF1, human phage antibodies may be selected by binding to EBV-infected and transformed (tumour) cells directly.

Therefore, it was the aim to demonstrate this possibility by analysing the specific enrichment of loop-specific peptide reactive human antibody phages by subsequent selection on intact viable EBV-transformed B-cells.

Building on the results of example 3, only LMP1-specific data are shown in this example.

Methods

Screening and Selection of the Phages Using JY Cells:

$3*10^6$ JY-cells/ml were taken up in PBS containing 10% FCS and 2% marvel and incubated at RT for 30 minutes under constant agitation. At the same time the phages were incubated in PBS containing 10% FCS and 2% Marvel for 30 minutes at RT. Cells were subsequently centrifuged at 500×g for 5 minutes and the cell pellets were mixed with the phages for 1 hr under constant agitation at RT. The cells were centrifuged and washed 10× with PBS. After washing the cells were resuspended in 600 µl water and phages were eluted by adding 600 µl of tri-ethylamine (TEA) to the cells and incubation for 5 minutes at RT. The TEA was neutralized by adding 600 µl 1 M TRIS-HCl (pH=7,4) to the suspension. Cell debris and phages were separated by centrifugation at 1000×g for 5 minutes. The supernatant containing the selected phages was stored at 4° C. until further use.

Results:

For the selection of phages reactive with natural LMP1 as expressed on the surface of JY cells, phage populations from round 2 of the selection on synthetic peptides were used. These phages showed no significant enrichment as shown in Table 3.

Table 5 summarises the results of the subsequent selection rounds for phage populations preselected on either LMP1 loop-1,-2 and -3 specific peptides.

TABLE 5

Result of the phage selection on JY-cells.

| Round | Input | Output | o/i-ratio | Enrichment |
|---|---|---|---|---|
| Loop 1 | | | | |
| 3 | $2.4 * 10^{13}$ | $2.4 * 10^6$ | $1.0 * 10^{-7}$ | — |
| 4 | $1.4 * 10^{13}$ | $2.4 * 10^8$ | $1.7 * 10^{-5}$ | 170 |
| Loop 2 | | | | |
| 3 | $2.0 * 10^{13}$ | $2.7 * 10^6$ | $1.4 * 10^{-7}$ | — |
| 4 | $2.8 * 10^{13}$ | $7.0 * 10^7$ | $2.5 * 10^{-7}$ | 1 |
| Loop 3 | | | | |
| 3 | $2.0 * 10^{13}$ | $1.0 * 10^6$ | $5.0 * 10^{-8}$ | — |
| 4 | $1.8 * 10^{13}$ | $9.1 * 10^7$ | $5.4 * 10^{-6}$ | 108 |

For LMP1 loop 1 and loop 3 good enrichment was found after round 4, however no enrichment was found for loop 2.

This was to be expected because loop 2 is the smallest peptide (protein-part) and selection on peptides also gave the lowest level of enrichment (Table 3).

From the selection of round 4 on JY cells, 96 colonies were picked from both loop1 and loop 3 phages, induced for phage production and subsequently analysed in peptide ELISA using the bio-NHS-labelled peptides.

For LMP1 loop-1, 8/96 JY-selected phages were reactive against the peptides of loop-1. For LMP1 loop-3, 28/96 JY-selected phages were reactive against loop-3 peptides and several were also reactive against the circular peptide of loop-3.

FIG. 9 gives an example of these ELISA results.

For loop 2 no specific phages were found which was expected because no enrichment was found after round four of selection.

In general, the ELISA reactivity with the peptides was lower compared to the response after phage selection using peptides (see example 3).

The peptide-binding affinity of the phages selected on native LMP1 expressed on the surface of viable JY cells may well be reduced compared to the binding affinity of phages directly selected to peptide-domains derived from LMP1 loop 1, 2 and 3. This may be related to minor changes in conformation between synthetic peptide and natural loop domains in the full length membrane-associated protein.

Further analysis of the phages reactive with LMP1 loop1 and/or loop 3 peptides revealed that many phage colonies had different fingerprints as was previously found for the peptide-selected phages and as indicated in example 3.

These data are summarized in Table 6.

TABLE 6

Summary of selections on JY cells.

| LMP1 loop peptide | Positive Clones | Different fingerprints |
|---|---|---|
| 1 | 8 | 4 |
| 2* | — | — |
| 3 | 29 | 5 |

*result after selection round 5.

These data show that human antibody reagents can be made by phage selection on native LMP1, LMP2 or BARF1 expressed on the surface of EBV-transformed cells.

---

What is claimed is:

1. An isolated cell expressing a peptide of less than 100 amino acids comprising an extracellular epitope of Epstein-Barr virus (EBV) encoded latent membrane protein, wherein the peptide comprises SEQ ID NO: 3.

2. An immunogenic composition comprising the isolated cell according to claim 1.

3. An isolated peptide comprising SEQ ID NO: 3, wherein the peptide has less than 100 amino acids.

4. A hybrid protein or fusion protein comprising the peptide according to claim 3.

5. The isolated cell of claim 1, wherein the peptide is in circular form.

6. The isolated peptide of claim 3, wherein the peptide is in circular form.

7. The according to claim 2, further comprising one or more peptides selected from the group of peptides comprising SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and/or SEQ ID NO: 13.

8. An immunogenic composition comprising the isolated peptide according to claim 3.

9. The immunogenic composition according to claim 8, further comprising one or more peptides selected from the group of peptides comprising SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and/or SEQ ID NO: 13.

* * * * *

UNITED STATES PATENT AND TRADEMARK OFFICE
CERTIFICATE OF CORRECTION

PATENT NO. : 8,241,639 B2
APPLICATION NO. : 12/857930
DATED : August 14, 2012
INVENTOR(S) : Middeldorp Page 1 of 1

It is certified that error appears in the above-identified patent and that said Letters Patent is hereby corrected as shown below:

On the title page, item [63]:

Now reads: "Continuation of application No. 11/284,879, filed on Nov. 22, 2005, now Pat. No. 7,811,581"

Should read: -- Continuation of U.S. application Ser. No. 11/284,879 filed on Nov. 22, 2005, which has issued as U.S. Patent No. 7,811,581, which is a continuation of, and claims priority to, U.S. Application No. 10/470,753 filed on Dec. 12, 2003, now abandoned, which itself claims priority from PCT/EP02/00997 having an international filing date of January 30, 2002. --

Column 1, line 8: after the Title and Cross Reference to Related Applications:

Now reads: "The present application is a continuation of U.S. application Ser. No. 11/284,879 filed Nov. 22, 2005 which has issued as U.S. Patent No. 7,811,581, which claims priority to U.S. Application No. 10/470,753 entitled, "METHOD FOR THE IDENTIFICATION OF EPSTEIN BARR VIRUS (EBV) TUMOR-ASSOCIATED LATENT MEMBRANE PROTEINS AND FOR SELECTION OF ANTIBODY REAGENTS REACTIVE THEREWITH," filed on Dec. 12, 2003, now abandoned, which itself claims priority from PCT/EP02/00997 having an international filing date of January 30, 2002."

Should read: -- The present application is a continuation of U.S. application Ser. No. 11/284,879 filed on Nov. 22, 2005, which has issued as U.S. Patent No. 7,811,581, which is a continuation of, and claims priority to, U.S. Application No. 10/470,753 filed on Dec. 12, 2003, now abandoned, which itself claims priority from PCT/EP02/00997 having an international filing date of January 30, 2002. --

Signed and Sealed this
Twenty-seventh Day of August, 2013

Teresa Stanek Rea
*Acting Director of the United States Patent and Trademark Office*

SEQUENCE LISTING

<160> NUMBER OF SEQ ID NOS: 18

<210> SEQ ID NO 1
<211> LENGTH: 12
<212> TYPE: PRT
<213> ORGANISM: Epstein Barr Virus

<400> SEQUENCE: 1

Val Met Ser Asp Trp Thr Gly Gly Ala Leu Leu Val
1               5                   10

<210> SEQ ID NO 2
<211> LENGTH: 11
<212> TYPE: PRT
<213> ORGANISM: Epstein Barr Virus

<400> SEQUENCE: 2

Ala Leu Trp Asn Leu His Gly Gln Ala Leu Phe
1               5                   10

<210> SEQ ID NO 3
<211> LENGTH: 12
<212> TYPE: PRT
<213> ORGANISM: Epstein Barr Virus

<400> SEQUENCE: 3

Tyr Leu Gln Gln Asn Trp Trp Thr Leu Leu Val Asp
1               5                   10

<210> SEQ ID NO 4

```
<211> LENGTH: 11
<212> TYPE: PRT
<213> ORGANISM: Epstein Barr Virus

<400> SEQUENCE: 4

Ala Ala Ser Cys Phe Thr Ala Ser Val Ser Thr
1               5                   10

<210> SEQ ID NO 5
<211> LENGTH: 20
<212> TYPE: PRT
<213> ORGANISM: Epstein Barr Virus

<400> SEQUENCE: 5

Leu Thr Trp Arg Ile Glu Asp Pro Pro Phe Asn Ser Leu Leu Phe Ala
1               5                   10                  15

Leu Leu Ala Ala
            20

<210> SEQ ID NO 6
<211> LENGTH: 9
<212> TYPE: PRT
<213> ORGANISM: Epstein Barr Virus

<400> SEQUENCE: 6

Leu Gln Leu Ser Pro Leu Leu Gly Ala
1               5

<210> SEQ ID NO 7
<211> LENGTH: 8
<212> TYPE: PRT
<213> ORGANISM: Epstein Barr Virus

<400> SEQUENCE: 7

Leu Gly Thr Leu Asn Leu Thr Met
1               5

<210> SEQ ID NO 8
<211> LENGTH: 18
<212> TYPE: PRT
<213> ORGANISM: Epstein Barr Virus

<400> SEQUENCE: 8

Leu Gln Thr Asn Phe Lys Ser Leu Ser Ser Thr Glu Phe Ile Pro Asn
1               5                   10                  15

Leu Phe

<210> SEQ ID NO 9
<211> LENGTH: 11
<212> TYPE: PRT
<213> ORGANISM: Epstein Barr Virus

<400> SEQUENCE: 9

Val Met Ser Asn Thr Leu Leu Ser Ala Trp Ile
1               5                   10

<210> SEQ ID NO 10
<211> LENGTH: 40
<212> TYPE: PRT
<213> ORGANISM: Epstein Barr Virus

<400> SEQUENCE: 10

Leu Gly Pro Glu Ile Glu Val Ser Trp Phe Lys Leu Gly Pro Gly Glu
1               5                   10                  15
```

```
Glu Gln Val Leu Ile Gly Arg Met His His Asp Val Ile Phe Ile Glu
            20                  25                  30

Trp Pro Phe Arg Gly Phe Phe Asp
        35                  40

<210> SEQ ID NO 11
<211> LENGTH: 75
<212> TYPE: PRT
<213> ORGANISM: Epstein Barr Virus

<400> SEQUENCE: 11

Ile His Arg Ser Ala Asn Thr Phe Phe Leu Val Val Thr Ala Ala Asn
1               5                   10                  15

Ile Ser His Asp Gly Asn Tyr Leu Cys Arg Met Lys Leu Gly Glu Thr
            20                  25                  30

Glu Val Thr Lys Gln Glu His Leu Ser Val Val Lys Pro Leu Thr Leu
        35                  40                  45

Ser Val His Ser Glu Arg Ser Gln Phe Pro Asp Phe Ser Val Leu Thr
    50                  55                  60

Val Thr Cys Thr Val Asn Ala Phe Pro His Pro
65                  70                  75

<210> SEQ ID NO 12
<211> LENGTH: 34
<212> TYPE: PRT
<213> ORGANISM: Epstein Barr Virus

<400> SEQUENCE: 12

His Val Gln Trp Leu Met Pro Glu Gly Val Glu Pro Ala Pro Thr Ala
1               5                   10                  15

Ala Asn Gly Gly Val Met Lys Leu Lys Asp Gly Ser Leu Ser Val Ala
            20                  25                  30

Val Asp

<210> SEQ ID NO 13
<211> LENGTH: 33
<212> TYPE: PRT
<213> ORGANISM: Epstein Barr Virus

<400> SEQUENCE: 13

Leu Ser Leu Pro Lys Pro Trp His Leu Pro Val Thr Cys Val Gly Lys
1               5                   10                  15

Asn Asp Lys Glu Glu Ala His Gly Val Tyr Val Ser Gly Tyr Leu Ser
            20                  25                  30

Gln

<210> SEQ ID NO 14
<211> LENGTH: 21
<212> TYPE: PRT
<213> ORGANISM: Epstein Barr Virus
<220> FEATURE:
<223> OTHER INFORMATION: LMP1 Epstein Barr Virus Protein

<400> SEQUENCE: 14

Cys Leu Leu Asp Val Leu Leu Thr Trp Trp Asn Gln Gln Leu Tyr Leu
1               5                   10                  15

Ala Cys Lys Lys Lys
            20

<210> SEQ ID NO 15
<211> LENGTH: 16
```

```
<212> TYPE: PRT
<213> ORGANISM: Epstein Barr Virus
<220> FEATURE:
<223> OTHER INFORMATION: LMP1 Epstein Barr Virus Protein

<400> SEQUENCE: 15

Leu Leu Asp Val Leu Leu Thr Trp Trp Asn Gln Gln Leu Tyr Leu Ala
1               5                   10                  15

<210> SEQ ID NO 16
<211> LENGTH: 28
<212> TYPE: PRT
<213> ORGANISM: Epstein Barr Virus
<220> FEATURE:
<223> OTHER INFORMATION: LMP2 Epstein Barr Virus Protein

<400> SEQUENCE: 16

Cys Met Gly Phe Leu Asn Pro Ile Phe Glu Thr Ser Ser Leu Ser Lys
1               5                   10                  15

Phe Asn Thr Gln Leu Ile Ser Gly Cys Lys Lys Lys
            20                  25

<210> SEQ ID NO 17
<211> LENGTH: 23
<212> TYPE: PRT
<213> ORGANISM: Epstein Barr Virus
<220> FEATURE:
<223> OTHER INFORMATION: LMP2 Epstein Barr Virus Protein

<400> SEQUENCE: 17

Asn Gly Phe Leu Asn Pro Ile Phe Glu Thr Ser Ser Leu Ser Lys Phe
1               5                   10                  15

Asn Thr Gln Leu Ile Ser Gly
            20

<210> SEQ ID NO 18
<211> LENGTH: 7
<212> TYPE: PRT
<213> ORGANISM: Epstein Barr Virus
<220> FEATURE:
<223> OTHER INFORMATION: LMP1 Epstein Barr Virus

<400> SEQUENCE: 18

Leu Ala Leu Leu Phe Trp Leu
1               5
```